(12) United States Patent
Viladot Petit et al.

(10) Patent No.: US 9,708,757 B2
(45) Date of Patent: Jul. 18, 2017

(54) PROCESS OF TREATMENT OF FIBERS AND/OR TEXTILE MATERIALS

(75) Inventors: Josep Lluis Viladot Petit, Barcelona (ES); Raquel Delgado Gonzalez, Gava Barcelona (ES); Alfonso Fernández Botello, Malaga (ES)

(73) Assignee: Lipotec, S.A., Gava (ES)

(*) Notice: Subject to any disclaimer, the term of this patent is extended or adjusted under 35 U.S.C. 154(b) by 602 days.

(21) Appl. No.: 13/636,989

(22) PCT Filed: Mar. 24, 2011

(86) PCT No.: PCT/EP2011/001474
§ 371 (c)(1),
(2), (4) Date: Nov. 29, 2012

(87) PCT Pub. No.: WO2011/116962
PCT Pub. Date: Sep. 29, 2011

(65) Prior Publication Data
US 2013/0064876 A1    Mar. 14, 2013

(30) Foreign Application Priority Data
Mar. 24, 2010 (ES) .................. 201030432

(51) Int. Cl.
*B05D 5/00* (2006.01)
*A61P 17/00* (2006.01)
*A61K 9/70* (2006.01)
*A61K 8/11* (2006.01)
*D06M 23/12* (2006.01)
*B01J 13/10* (2006.01)
*B01J 13/20* (2006.01)
*B01J 13/22* (2006.01)
*A61K 9/00* (2006.01)

(52) U.S. Cl.
CPC .............. *D06M 23/12* (2013.01); *A61K 8/11* (2013.01); *B01J 13/10* (2013.01); *B01J 13/206* (2013.01); *B01J 13/22* (2013.01); *A61K 9/0014* (2013.01); *A61K 2800/412* (2013.01)

(58) Field of Classification Search
None
See application file for complete search history.

(56) References Cited

U.S. PATENT DOCUMENTS

| | | | |
|---|---|---|---|
| 2,800,457 | A | 7/1957 | Green et al. |
| 4,774,231 | A | 9/1988 | Petitou et al. |
| 5,192,741 | A | 3/1993 | Orsolini et al. |
| 6,916,490 | B1 * | 7/2005 | Garver et al. ............. 424/489 |
| 2003/0044469 | A1 | 3/2003 | Viladot Petit et al. |
| 2003/0064106 | A1 | 4/2003 | Garces et al. |
| 2004/0151778 | A1 | 8/2004 | Richard et al. |
| 2005/0150056 | A1 | 7/2005 | Copete Vidal et al. |

FOREIGN PATENT DOCUMENTS

| | | | |
|---|---|---|---|
| EP | 0052510 | 5/1982 | |
| EP | 0064012 | 11/1982 | |
| EP | 0211610 | 2/1987 | |
| EP | 0277428 | 8/1988 | |
| EP | 0334586 | 9/1989 | |
| EP | 0346879 | 12/1989 | |
| EP | 0375388 | 6/1990 | |
| EP | 0403238 | 12/1990 | |
| EP | 1837074 | 9/2007 | |
| ES | 2009346 | 9/1989 | |
| JP | 5020084 | 3/1975 | |
| JP | 2003001100 | 1/2003 | |
| WO | 0141915 | 6/2001 | |
| WO | WO01/41915 A1 * | 6/2001 | .............. B01J 13/20 |
| WO | WO 0141915 A1 * | 6/2001 | |
| WO | 0166240 | 9/2001 | |
| WO | 02092217 | 11/2002 | |
| WO | 2005105290 | 11/2005 | |

OTHER PUBLICATIONS

"Microencapsulation of tamoxifen: Application to cotton fabric," Ma, Z.-H., et al., Colloids and Surfaces B: Biointerfaces 69: 85-90 (2009).*
International Search Report for PCT/EP2011/001474, Completed by the European Patent Office on Jun. 22, 2011, 2 Pages.
Chao-Xia et al. Color. Technol. 2004, vol. 120, p. 14-18, "Anchoring B-cyclodextrin to retain fragrances on cotton by means of heterobifunctional reactive dyes."
Nelson. International Journal of Pharmaceutics 2002, vol. 242, p. 55-62, "Application of microencapsulation in Textiles."
Malcolm et al. Journal of Controlled Release 2004, vol. 97, p. 313-320, "Controlled release of a model antibacterial drug from a novel self-lubricating silicone biomaterial."
Hu et al. Biomactromolecules 2006, vol. 7, No. 8, p. 2327-2330, "Encapsulation of Drug Reservoirs in Fibers by Emulsion Electrospinning: Morphology Characterization and Preliminary Release Assessment."
Schaab. Happi May 1986, p. 84-86, "Impregnating Fabrics with Mictrocapsules."
Jalon et al. European Journal of Pharmaceutics and Biopharmaceutics 2003, vol. 56, p. 183-187, "Increased efficacy of acyclovir-loaded microparticles against herpes simplex virus type 1 in cell culture."
Gottschalck et al. Internation Cosmetic Ingredient Dictionary and Handbook 12th edition 2008, vol. 3, 14 Pages.
Rodrigues et al. Ind. Eng. Chem. Res. 2008, vol. 47, No. 12, p. 4142-4147, "Microencapsulation of Limonene for Textile Application."
Sliwka. Angew Chem. Internat. Edit. 1975, vol. 14, No. 8, p. 539-550, "Microencapsulation."

(Continued)

*Primary Examiner* — David J Blanchard
*Assistant Examiner* — Daniel F Coughlin
(74) *Attorney, Agent, or Firm* — Fay Sharpe LLP

(57) ABSTRACT

A process of treatment of textile materials containing microcapsules of active ingredients, the fibers and/or textile materials resulting from this process and their cosmetic or pharmaceutical use and/or their use as a repellent.

14 Claims, 1 Drawing Sheet

(56) References Cited

OTHER PUBLICATIONS

Augustin et al. Chemical Society Reviews 2009, vol. 38, p. 902-912, "Nano- and micro-structured assemblies for encapsulation of food ingradients."
Drusch et al. Trends in Food Science & Technology 2009, vol. 20, p. 237-244, "Patent-based review on inductrial approaches for the microencapsulation of oils rich in polyunsaturated fatty acids."
Monllor et al. Textile Research Journal 2009, vol. 79, p. 365-380, "Thermal Behavior of Microencapsulated Fragrances on Cotton Fabrics."
Zurich. Current Problems in Dermatology 2006, vol. 33, 10 Pages. "Biofunctional Textiles and the Skin."

* cited by examiner

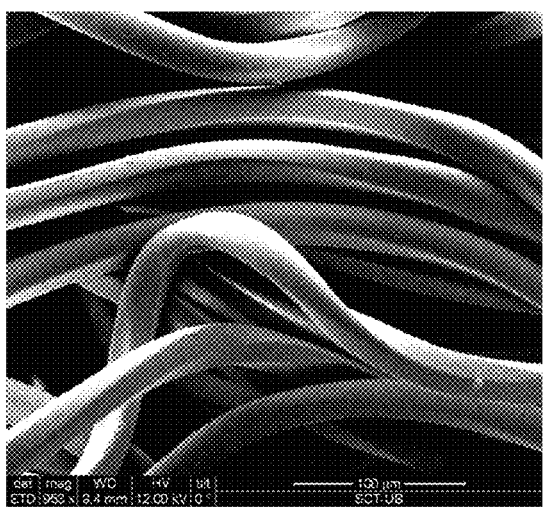
a)
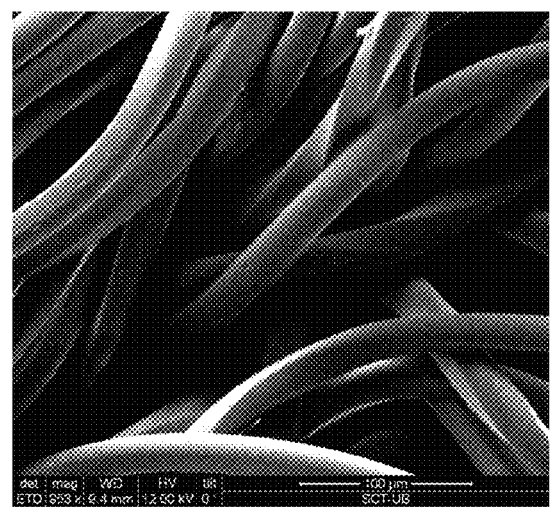
d)
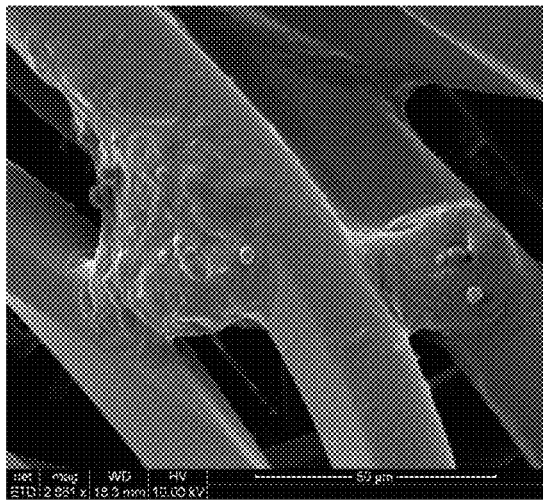
b)
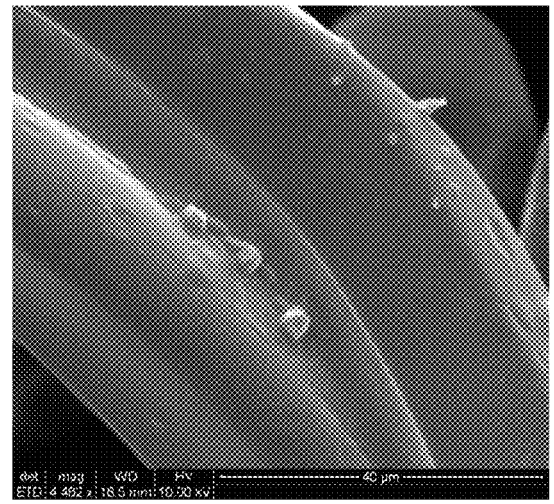
e)
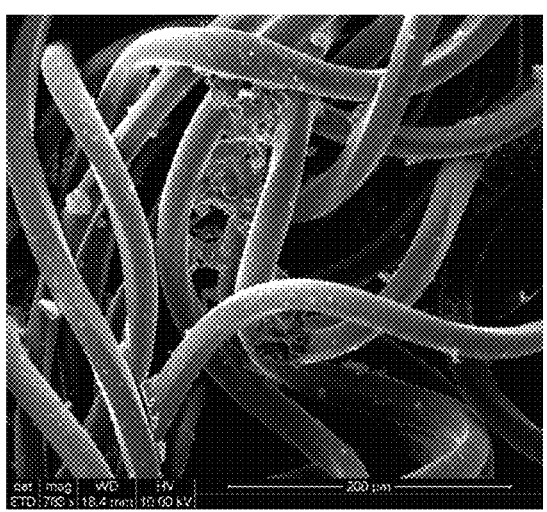
c)
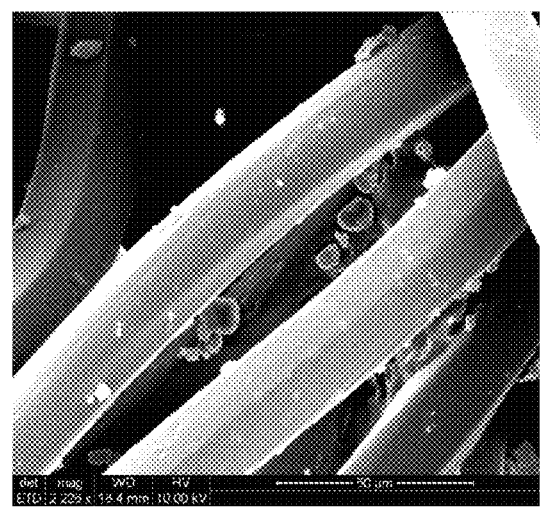
f)

PROCESS OF TREATMENT OF FIBERS AND/OR TEXTILE MATERIALS

CROSS-REFERENCE TO RELATED APPLICATION

This application is the U.S. national phase of PCT Appln. No. PCT/EP2011/001474 filed on Mar. 24, 2011, which claims priority to Spanish Patent Application No. 201030432 filed on Mar. 24, 2010, the disclosures of which are incorporated in their entirety by reference herein.

FIELD OF THE INVENTION

This invention is found within the field of the encapsulation of active ingredients and the treatment of textile materials. In particular it relates to a process of treatment of textile materials, and their cosmetic or pharmaceutical use or their use as an insect repellent.

PRIOR ART

In the prior art there are different techniques for encapsulation of cosmetic and/or pharmaceutical active ingredients in microcapsules. Encapsulation techniques consist of the coating of active ingredients which are useful in different fields such as cosmetics, pharmacy or food in the form of different natured polymers to obtain particles of a size comprised between 1 μm and 1 mm. [E. G. JalonDe, M. J. Blanco-Prieto, P. Ygartua, and S. Santoyo. *Eur. J. Pharm. Biopharm.* 56:183-187 (2003); M. A. Augustin and Y. Hemar. *Chem. Soc. Rev.,* 2009, 38, 902-912; Sofia N. Rodrigues, Isabel Fernandes, Isabel M. Martins, Vera G. Mata, Filomena Barreiro, and Alirio E. Rodrigues. *Ind. Eng. Chem. Res.* 2008, 47 (12), 4142-4147; Stephan Drusch and Saverio Mannino. *Trends in Food Science & Technology* 2009, 20, 237-244]. A microcapsule has a relatively simple morphological structure, and is comprised by two clearly differentiated elements, a nucleus which contains one or several active ingredients and a polymeric coating which surrounds the nucleus and thus protects the active ingredients from the outside [W. Sliwka. *Angew. Chem. Internat. Edit.* 14, 539 (1975)].

Within the processes for encapsulation of active ingredients, one of the most common is encapsulation by a coacervation process, which can be simple or complex coacervation. Coacervation is based on the insolubilization of a polymer in a colloidal system by a coacervate particle deposition process which encapsulates at least one active ingredient in their interior. Amongst the mechanisms which induce the decrease in solubility, and consequently, the deposition of the coacervate, are changes in temperature, modifications to the pH, addition of a nonsolvent of the polymer, of a salt or an incompatible polymer. Initially, the active ingredient which is to be encapsulated is dispersed in liquid or solid form in a solution of the polymer or polymers which form the coating. Afterwards the formation of the coacervate of the polymer or polymers is induced by one of the previous mechanisms, followed by its deposition on the active ingredient. The continual deposition of the polymer is brought about a reduction in the system's free energy, due to a reduction of the surface area during the coalescence of the polymeric coacervate which results in the formation of a continual coating around the encapsulated active ingredient. Next, the hardening of the polymeric coating of the coacervate is carried out, in a process known as cross-linking, by the addition of a cross-linking agent, and optionally cooling the system down. Finally, the separation of the microcapsules by centrifugation or filtration is carried out. As previously stated, there are two types of coacervation, simple and complex. Simple coacervation occurs when a nonsolvent of the polymer is added to the system, generally a very hydrophilic substance, which causes the separation in two phases with the formation of the coacervate. Examples of this procedure are described in documents such as ES 2009346, EP 052510 A1, and EP 0346879 A1. Complex coacervation is achieved when two colloidal substances with an opposite electric charge interact producing a complex which has a lesser solubility than that of the separate colloids and which is deposited on the active ingredient to be encapsulated forming a membrane which isolates the active ingredient. Examples of this procedure are described in documents such as WO 02/092217, WO 2005/105290, EP 1261421 A1 and EP 18737074 A1. Complex coacervation is very dependent on the pH, since the electrostatic interaction between the two colloidal substances is carried out with a pH range in which one of the colloidal substances is in its acidic cationic form, and the other colloidal substance in its basic anionic form.

One of the microencapsulation applications which has stirred up great interest in recent years is the treatment of fibers and textile materials in order to improve their aspect, shine, color, smell and elasticity or to provide new the fiber or textile material with functionalities such as the treatment and/or care of the skin, scalp and/or hair. Microencapsulation is a solution often used to bind the encapsulated active ingredient to the fiber or textile material since it enables to prolong the permanence of the active ingredient in the fiber or textile material, and which is slowly released onto the skin, scalp and/or hair by degradation of the microcapsules by pressure, heat, friction, osmosis or body moisture. Thus a continual release of active ingredients onto the skin, scalp and/or hair is achieved through the textile materials.

In the prior art there are different types of binding or link of microcapsules to fibers or textile materials, for example, one of the types of binding consists of the binding of microcapsules to fibers or textile materials through covalent bonds [W. Chao-Xia and C. Shui-Lin, *Coloration Technology* 2004, 120, 14-18]. In a typical embodiment, the microcapsule coating is formed by cyclodextrins, and preferably, the encapsulated active ingredients are perfumes or odor-trapping agents. The fact that the microcapsules are bound or linked covalently makes them remain on the fibers or textile materials, and the microcapsules of the active ingredient to be encapsulated can be reloaded. The principal problem presented by this type of binding is that the creation of covalent bonds entails a modification to the chemical structure of the fiber, which can lead to degradation to and breakage of the textile material.

Another type of binding or link of microcapsules to fibers or textile materials consists of the manufacture of fibers in solutions wherein the microcapsules containing the active ingredients which are to be fixed to the fibers are already present [Qi, Ping Hu, Jun Xu, and Wang *Biomacromolecules,* 2006, 7 (8), 2327-2330]. It is a type of binding or link which is limited solely to active ingredients which should not pass through to the skin, such as insect repellents, and which, therefore, excludes any type of cosmetically and/or pharmaceutically used active ingredient.

A last type of binding or link of microcapsules to fibers or textile materials is through ionic bonds between the microcapsule and the fibers [P. Monllor, L. Sánchez, F. Cases and M. A. Bonet, *Textile Research Journal* 2009, 79, 365-380]. The binding is caused by electrostatic interaction between the negative charges of the fibers of the textile materials and the microcapsules which have previously been cationized. The principal advantages of this type of binding or link over the previous types are that it is not limited to one type of active ingredient and that this type of binding to the fibers or textile materials is not detrimental to the mechanical properties of the textile material as in the case of covalent binding. In addition, and also unlike the previous types of binding of microcapsules containing active ingredients to textile materials, there is the possibility of the final consumer reloading the textile material with microencapsulated active ingredients himself.

However, one of the problems that arises for the fibers or textile materials containing active ingredients is the low washproofness both of the microcapsules which contain the active ingredients, as well as the low permanence of the active ingredients in the microcapsules when they come into contact with the surfactants of the washing agents of textile materials. The surfactants of the washing agents which are used to dissolve the dirt particles in textile materials are also capable of penetrating the microcapsules which are bound or linked to the textile material and cause the solving of the active ingredient which was encapsulated by pulling it out of the textile material. Likewise, the low washproofness causes the microcapsules, and consequently the active ingredient, are lost during washing without the active ingredient being transferred to the skin, scalp and/or hair. Both the low washproffness of the microcapsules bound to the fibers or textile materials and the permanence of the active ingredients in the microcapsules are deeply related to the binding or link processes of the microcapsules to the fibers or textile materials, as well as the microcapsule preparation processes.

However, none of the types of binding of microcapsules to previous fibers or textile materials known in the prior art enable the encapsulated active ingredient to remain in the textile material for an acceptable number of washes. Therefore, there is a need in the prior art of a process for the treatment of textile materials which resolves the aforementioned problems.

The Japanese patent request JP 50-20084 describes a process for binding microcapsules containing dyes to fabrics. The microcapsules described in the aforementioned document are prepared by a coacervation process, wherein once the coacervate is formed at pH 4.5, the cross-linking of the coacervate is carried out at pH 9. However, there are no indications in this document that the increase of the pH at the cross-linking step enables microcapsules bound to the textile material to be obtained and the active ingredient contained in them to resist a certain number of washes. In addition, the size of the microcapsules formed in this document, from 100 to 300 μm in diameter, greatly hinders the binding of the microcapsules to the textile material, as well as obtaining a regular distribution of them throughout the textile material and a good permanence of the microcapsules in the textile material. On the other hand, this increased size of the microcapsules does not avoid the surfactant of the washing agents of textile materials entering into the microcapsules and solubilizing the active ingredient and pulling it out of the textile material.

Likewise, document U.S. Pat. No. 2,800,457 describes a process of complex coacervation for microcapsules, wherein the pH is optionally increased before cross-linking the microcapsules formed. However, in this document, it is not considered that the microcapsules formed by this process can be bound to fibers or textile materials, not to mention that the microcapsules in the textile material obtained could still be bound to the textile material after drying at temperatures above 100° C.

Surprisingly, the inventors of this invention have found a process for the treatment of textile materials containing at least one active ingredient bound to fibers and/or textile materials in which an increase in pH once the microcapsule coacervates have been formed and before their cross-linking, enables to obtain fibers and/or textile materials containing at least one active ingredient wherein the active ingredient remains in the fibers and/or textile materials for an acceptable number of washes.

DESCRIPTION OF THE INVENTION

This invention relates to a process for the treatment of fibers and/or textile materials which resolves the previously described problems.

According to a first aspect, this invention describes a process of treatment of fibers and/or textile materials containing at least one active ingredient that comprises the following steps:
 a) dissolution of two hydrophilic colloids in a solvent in which they are soluble and addition of at least one active ingredient to form a suspension of the active ingredient in this solution,
 b) adjusting the pH and/or diluting the previous suspension to cause the coacervation of the colloids and their deposition on the active ingredient which is thus encapsulated,
 c) increasing the pH of the suspension and adding a crosslinking agent to harden the microcapsules formed,
 d) cationizing the microcapsules with a polymer or a cationic monomer,
 e) linking or binding of the microcapsules to the fibers and/or textile materials,
 f) drying of the fibers and/or textile materials.

The order of the steps is consecutive a), b), c), d), e) and f). Optionally, between steps b) and c) there is an intermediate step of cooling of the microcapsules obtained in step b). This process of treatment of fibers and/or textile materials enables a regular distribution of microcapsules is obtained over the whole surface of the fiber and/or textile material due to the small size of the microcapsules. Furthermore, this small size of the microcapsules also results in a greater penetration of the microcapsules into the fiber and/or textile material, which leads to a greater permanence after the washes. On the other hand, the polymeric coating of the microcapsules formed by the hydrophilic colloids is extremely rigid and compact which makes the microcapsules stable after drying the fiber and/or textile material.

In the context of this invention, the treatment of fibers and/or textile materials enables fibers and/or textile materials are obtained with functional characteristics such as cosmetic, pharmaceutical or insect repellents.

In a particular embodiment, the two hydrophilic colloids are selected, without restriction, from the group formed by proteins, polysaccharides, polyesters, polyacrylates, polycyanoacrylates, polyethylene glycol, copolymers and/or mixtures thereof. Preferably, the proteins and polysaccharides are selected, for example and not restricted to, from the group formed by gelatin, albumin, β-lactoglobulin, whey protein, pea protein, potato protein, broad bean protein, wheat protein, bovine serum albumin, poly-L-lysine, soy protein, caseinates, casein, soy glycine, sodium alginate, wheat starch, corn starch, methyl cellulose, ethyl cellulose, hydroxypropyl methyl cellulose (HPMC), cellulose nitrate, carboxymethyl cellulose, gum arabic, xanthan gum, mesquite gum, guar gum, carrageenans, tragacanth gum, arabinogalactans, galactomannans, sodium hexametaphosphate, exopolysaccharide B40, carboxymethyl sodium, pectin, methoxyl pectin, agar, dextran, chitosan, cellulose acetate butyrate, cellulose acetate phthalate, acrylic derivatives and polyesters such as poly-ε-caprolactone, zein, hydroxypropyl methylcellulose phthalate, hydroxypropyl methylcellulose acetate succinate, polyvinyl acetate phthalate, poly(p-dioxanone), poly(δ-valerolactone), poly(β-hydroxybutyrate), poly(β-hydroxybutyrate) and β-hydroxyvalerate copolymers, poly(β-hydroxypropionate), methylacrylic acid copolymers (Eudragit® L and S), dimethylaminoethyl methacrylate copolymers (Eudragit® E), trimethylammonium ethyl methacrylate copolymers (Eudragit® RL and RS), polymers and copolymers of lactic and glycolic acid, polymers and copolymers of lactic and glycolic acid and polyethylene glycol and mixtures thereof.

In another particular embodiment, the hydrophilic colloid solvent is water or an aqueous solution.

In another particular embodiment, step a) of the process of the invention is carried out at a temperature of preferably over 40° C., and more preferably at over 50° C.

In another particular embodiment, the adjustment to the pH in stage b) of the process of the invention depends on the combination of colloids used to form the coacervate, but preferably it is an acid pH, between 3 and 5.5, and more preferably between 4 and 5.

In another particular embodiment, the temperature at which the microcapsules are cooled between step b) and step c) is lower than 30° C., and preferably equal or lower than 10° C.

In another particular embodiment, the increase in pH in step c) of the process of the invention is a pH between 6.5 and 13, preferably a pH between 7 and 10.

In another particular embodiment, the crosslinking agent of step c) of the process of the invention is selected, for example and not restricted to, from the group formed by aldehydes such as glutaraldehyde or formaldehyde; transglutaminases, derivatives of methylenebisacrylamide, N,N-methylenebisacrylamide, N,N-(1,2-dihydroxyethylene)bisacrylamide, derivatives of ethylene glycol dimethacrylate, ethylene glycol diacrylate, diethylene glycol diacrylate, tetraethylene glycol diacrylate, ethylene glycol dimethacrylate, diethylene glycol dimethacrylate, triethylene glycol dimethacrylate, sodium tripolyphosphate, N-hydroxysuccinamide esters and/or imidoesters.

In another particular embodiment, the size of the microcapsules after cross-linking step c) is lower than 30 μm, preferably lower than 10 μm.

In another particular embodiment, the cationic polymer used to cationize the microcapsules in step d) of the process of the invention is selected, for example and not restricted to, from the group formed by cationic derivatives of cellulose, such as quaternized hydroxyethyl cellulose, which can be acquired under the name Polymer JR 400™ by Amerchol; cationic starches; diallyl ammonium and acrylamide salt copolymers; quaternized vinylpyrrolidone/vinylimidazole polymers such as Luviquat™ (BASF); condensation products of polyglycols and amines; polyquaternium polymers and copolymers; polymers called Merquats of polyquaternium-6, polyquaternium-7, polyquaternium-16, polyquaternium-10; polyquaternium-4 copolymers; dicocoylethylhydroxyethylammonium, grafting copolymers with a cellulose skeleton and quaternary ammonium groups; quaternized collagen polypeptides such as hydroxypropyllauryldimonium hydrolyzed collagen (Lamequat™ by Grünau); quaternized wheat polypeptides; polyethylenimine; cationic silicone polymers such as amidomethicone or quaternium-22 silicone; adipic acid and dimethylamino hydroxypropyl diethylenetriamine copolymers (Cartaretine™ by Sandoz); acrylic acid copolymers with dimethyldiallylammonium chloride (Merquat™ 550 by Chemviron); cationic chitin derivatives such as chitosan and its derivatives; condensation products of cationic dihalogen alkylene such as dibromobutane with bisdialkylamines; bis-dimethylamino-1,3-propane; derivatives of cationic guar gum such as guarhydroxypropyltrimonium, Jaguar™ CBS, Jaguar™ C-17, Jaguar™ C-16 by Celanese; quaternary ammonium salt polymers such as Mirapol™ A-15, Mirapol™ AD-1, Mirapol™ AZ-1 by Miranol; quaternized polysaccharide polymers of natural derivatives such as azarose; cationic proteins selected from gelatin, gum arabic; cationic polymers from the group formed by polyamides, polycyanoecrylates, polylactides, polyglycolides, polyaniline, polypyrrole, polyvinylpyrrolidone, amino silicone polymers and copolymers, polystyrene, polyvinyl alcohol, polystyrene and maleic acid anhydride copolymers, methyl vinyl ether, epoxy resins and styrene and methyl methacrylate copolymers; dimethylamino methacrylate, cationic polyacrylates and polymethacrylates such as Eudragit™ RL 30 D by Röhm; polyamine derivatives optionally substituted by derivative polyethylene glycol members; polyamino acids under pH conditions wherein they are cationic; polyethyleneimine; quaternized derivatives of polyvinylpyrrolidone (PVP) and hydrophilic urethane polymers, as well as any mixture of the aforementioned cationic groups.

In another particular embodiment, the cationic polymer used to cationize the microcapsules in step d) of the process of the invention is selected, for example and not restricted to, from the group formed by dicocoylethyl hydroxyethylmonium methosulfate, cetrimonium chloride, distearoylethyl hydroxyethylmonium methosulfate, dipalmitoylethyl hydroxyethylmonium methosulfate, babassuamidopropalkonium chloride, trimonium acetamide propyl chloride, cetrimonium tosylate, oleamidopropyl hydroxysultaine, quaternium-22, quaternium-91, dilaureth-4 dimonium chloride, distearyldimonium chloride, PEG-5 hydrogenated tallow amine, trimethylsilyl propyl soy dimonium chloride, minoxidil, capryloyl glycine, hydroxypropyltrimonium hydrolyzed corn starch, cysteine chlorhydrate, biotin, carnitine, ceramide 2, ceramide 1, ceramide 6, alanine, cocamidoethyl betaine, cystine, cocodimonium hydroxypropyl hydrolyzed rice protein, DEA-isostearate, DEA-lauraminopropionate, disodium lauriminodiacetate.

In another particular embodiment, the linking or binding of the microcapsules to fibers and/or textile materials in step e) of the process of this invention is carried out by exhaustion bath, by foulard, or by spraying. In the context of this invention, the terms "binding" and "link" are used without distinction.

In another particular embodiment, the drying of the fibers and/or textile materials of this invention's process is carried out for at least 2 minutes at temperatures over 100° C., preferably equal to or higher than 120° C.

The process of this invention resolves the problem of the loss of active ingredient in the fibers and/or textile materials after being washed. The permanence of the active ingredient for an acceptable number of washes of the fibers and/or textile materials means that there is greater than 5% of active ingredient in the fibers and/or textile materials after 10 washes, and more preferably, more than 10% after 10 washes. The washing of the fibers and/or textile materials is carried out either by hand, according to standard ISO 105 C06 A1S, or by machine, according to standard UNE-EN 6330:2001.

The process of this invention can be applied to the fibers of textile materials before or after their manufacture, and it should be understood that binding to textile materials means binding to the fibers of the textile materials. The textile fibers can be natural or synthetic and are selected, for example and not restricted to, from the group formed by wool, cotton, silk, nylon, cellulose, polyamide or polyester, among others. In this invention textile materials are understood to be woven fabrics, non-woven fabrics, garments and medical devices. Examples of woven fabrics, non-woven fabrics, garments and medical devices can be found in the literature and are known in the prior art ("*Impregnating Fabrics With Microcapsules*", HAPPI May 1986; *Int. J. Pharm.* 2002, 242, 55-62; "*Biofunctional Textiles and the Skin*" *Curr. Probl. Dermatol.* 2006 v. 3; *J. Cont. Release* 2004, 97, 313-320). Among the textile materials the preferred woven fabrics, non-woven fabrics, garments and medical devices are bandages, gauzes, t-shirts, socks, tights, underwear, girdles, gloves, diapers, sanitary napkins, dressings, bedspreads, wipes, hydrogels, adhesive patches, non-adhesive patches, micro-electric patches and/or face masks.

In another particular embodiment, the active ingredient is selected from the group formed by active ingredients and/or cosmetic and/or dermopharmaceutical adjuvants and insect repellents. In particular, the active ingredients and/or cosmetic and/or dermopharmaceutical adjuvants are selected, for example and not restricted to, from the group formed by surfactants, humectants or substances which retain moisture, moisturizers or emollients, agents stimulating healing, coadjuvant healing agents, agents stimulating re-epithelialization, coadjuvant re-epithelialization agents, agents which synthesize dermal or epidermal macromolecules, firming and/or redensifying and/or restructuring agents, cytokine growth factors, agents which act on capillary circulation and/or microcirculation, anti-glycation agents, free radical scavengers and/or anti-atmospheric pollution agents, reactive carbonyl species scavengers, 5α-reductase-inhibiting agents, lysyl- and/or prolyl hydroxylase inhibiting agents, defensin synthesis-stimulating agents, bactericidal agents and/or bacteriostatic agents and/or antimicrobial agents and/or germicidal agents and/or fungicidal agents and/or fungistatic agents and/or germ-inhibiting agents, anti-viral agents, antiparasitic agents, antihistaminic agents, NO-synthase inhibiting agents, desquamation agents or keratolytic agents and/or exfoliating agents, comedolytic agents, anti-psoriasis agents, anti-dandruff agents, anti-inflammatory agents and/or analgesics, anesthetic agents, anti-wrinkle and/or anti-aging agents, cosmetic deodorants and/or absorbent and/or body odor masking deodorants, antiperspirant agents, perfuming substances and/or perfumed oils and/or isolated aromatic compounds, anti-oxidizing agents, agents inhibiting vascular permeability, hydrolytic epidermal enzymes, whitening or skin depigmenting agents, agents inhibiting sweat-degrading enzymes, agents capable of filtering UV rays, agents which stimulate or regulate keratinocyte differentiation, anti-itching agents, agents which stimulate or inhibit the synthesis of melanin, propigmenting agents, self-tanning agents, agents stimulating the proliferation of melanocytes, liquid propellants, vitamins, amino acids, proteins, biopolymers, gelling polymers, skin relaxant agents, agents capable of reducing or treating bags under eyes, agents for the treatment and/or care of sensitive skin, astringent agents, agents regulating sebum production, anti-stretch mark agents, lipolytic agents or agents stimulating lipolysis, venotonic agents, anti-cellulite agents, calming agents, agents acting on cell metabolism, agents to improve dermal-epidermal junction, agents inducing hair growth or hair-loss retardants, body hair growth inhibiting or retardant agents, heat shock protein synthesis stimulating agents, muscle relaxants, muscle contraction inhibiting agents, agents inhibiting the aggregation of acetylcholine receptors, anticholinergic agents, elastase inhibiting agents, matrix metalloproteinase, inhibiting agents, chelating agents, vegetable extracts, essential oils, marine extracts, mineral salts, cell extracts, emulsifying agents, agents stimulating the synthesis of lipids and components of the stratum corneum (ceramides, fatty acids, etc.), agents obtained from a biofermentation process and/or mixtures thereof. The nature of these active ingredients and/or cosmetic and/or alimentary adjuvants can be synthetic or natural, such as vegetable extracts, or come from a biotechnological process or from a combination of a synthetic process and a biotechnological process. Additional examples can be found in the *CTFA International Cosmetic Ingredient Dictionary & Handbook*, 12*th* *Edition* (2008). In the context of this invention, a biotechnological process is understood to be any process which produces the active ingredient, or part of it, in an organism, or in a part of it.

In a particular embodiment, the humectant or substance that retains moisture, moisturizer or emollient is selected, for example and not restricted to, from the group formed by polyols and polyethers such as glycerin, ethylhexylglycerin, caprylyl glycol, pentylene glycol, butylene glycol, propylene glycol and their derivatives, triethylene glycol, polyethylene glycol, Glycereth-26, Sorbeth-30; panthenol; pyroglutamic acid and its salts and derivatives; amino acids, such as serine, proline, alanine, glutamate or arginine; ectoine and its derivatives; N-(2-hydroxyethyl)acetamide; N-lauroyl-pyrrolidone carboxylic acid; N-lauroyl-L-lysine; N-alpha-benzoyl-L-arginine; urea; creatine; α- and β-hydroxy acids such as lactic acid, glycolic acid, malic acid, citric acid or salicylic acid, and their salts; polyglyceryl acrylate; sugars and polysaccharides, such as glucose, saccharide isomerate, sorbitol, pentaerythritol, inositol, xylitol, trehalose and derivatives thereof, sodium glucuronate, carraghenates (Chondrus crispus) or chitosan; glycosaminoglycans such as hyaluronic acid and derivatives thereof; aloe vera in any of its forms; honey; soluble collagen; lecithin and phosphatidylcholine; ceramides; cholesterol and its esters; tocopherol and its esters, such as tocopheryl acetate or tocopheryl linoleate; long-chain alcohols such as cetearyl alcohol, stearyl alcohol, cetyl alcohol, oleyl alcohol, isocetyl alcohol or octadecan-2-ol; long-chain alcohol esters such as lauryl lactate, myristyl lactate or $C_{12}$-$C_{15}$ alkyl benzoates; fatty acids such as stearic acid, isostearic acid or palmytic acid; polyunsaturated fatty acids (PUFAs); sorbitans such as sorbitan distearate; glycerides such as glyceryl monoricinoleate, glyceryl monostearate, glyceryl stearate citrate or caprylic and capric acid triglyceride; saccarose esters such as saccarose palmitate or saccarose oleate; butylene glycol esters, such as dicaprylate and dicaprate; fatty acid esters such as isopropyl isostearate, isobutyl palmitate, isocetyl stearate, isopropyl laurate, hexyl laurate, decyl oleate, cetyl palmitate, di-n-butyl sebacate, isopropyl myristate, isopropyl palmitate, isopropyl stearate, butyl stearate, butyl myristate, isopropyl linoleate, 2-ethylhexyl palmitate, 2-ethylhexyl cocoate, decyl oleate, myristyl myristate; squalene; mink oil; lanolin and its derivatives; acetylated lanolin alcohols; silicone derivatives such as cyclomethicone, dimethicone or dimethylpolysiloxane; Antarcticine® [INCI: *Pseudoalteromonas* Ferment Extract] or acetyl-glutamyl-methionyl-alanyl-isoleucine, acetyl-arginyl-phenylglycyl-phenylglycine or acetyl-arginyl-6-aminohexanoyl-alanine marketed by Lipotec, petrolatum; mineral oil; mineral and synthetic waxes; beeswax (cera alba); paraffin; or waxes and oils with vegetable origins such as candelilla wax (*Euphorbia cerifera*), carnauba wax (*Copernicia cerifera*), shea butter (*Butirospermum parkii*), cocoa butter (*Theobroma cacao*), castor oil (*Ricinus communis*), sunflower oil (*Helianthus annuus*), olive oil (*Olea europaea*), coconut oil (*Cocos nucifera*), palm oil (*Elaeis guineensis*), wheat germ oil (*Triticum vulgare*), sweet almond oil (*Prunus amygdalus dulces*), musk rose oil (*Rosa moschata*), soya bean oil (*Glycine soja*), grape seed oil (*Vitis vinifera*), calendula oil (*Calendula officinalis*), jojoba oil (*Simmonsis chinensis*), mango oil (*Mangifera indica*), avocado oil (*Persea gratissima*), and/or mixtures thereof, among others.

Likewise, in another particular embodiment, the agent stimulating healing, coadjuvant healing agent, agent stimulating re-epithelialization and/or coadjuvant re-epithelialization agent is selected, for example and not restricted to, from the group formed by extracts of *Aristoloquia clematis, Centella asiatica, Rosa moschata, Echinacea angustifolia, Symphytum officinale, Equisetum arvense, Hypericum perforatum, Mimosa tenuiflora, Persea gratisima, Prunus africanum, Tormentilla erectea, Aloe vera*, Polyplant® Epithelizing [INCI: *Calendula Officinalis, Hypericum Perforatum, Chamomilla Recutita, Rosmarinus Officinalis*] marketed by Provital, Cytokinol® LS 9028 [INCI: Hydrolyzed Casein, Hydrolyzed Yeast Protein, Lysine HCl] marketed by Laboratories Serobiologiques/Cognis or Deliner® [INCI: *Zea May* (Corn) Kernel Extract] marketed by Coletica/Engelhard/BASF, allantoin, cadherins, integrins, selectins, hyaluronic acid receptors, immunoglobulins, fibroblast growth factor, connective tissue growth factor, platelet-derived growth factor, vascular endothelial growth factor, epidermal growth factor, insulin-like growth factor, keratinocyte growth factors, colony-stimulating factors, transforming growth factor beta, tumor necrosis factor alpha, interferons, interleukins, matrix metalloproteinases, receptor protein tyrosine phosphatases, Antarcticine® [INCI: *Pseudoalteromonas* Ferment Extract], Decorinyl® [INCI: Tripeptide-10 Citrulline], Trylagen® [INCI: *Pseudoalteromonas* Ferment Extract, Hydrolyzed Wheat Protein, Hydrolyzed Soy Protein, Tripeptide-10 Citrulline, Tripeptide-1], acetyl-glutamyl-methionyl-alanyl-isoleucine, acetyl-arginyl-phenylglycyl-phenylglycine or acetyl-arginyl-6-amino-hexanoyl-alanine marketed by Lipotec, among others.

In a particular embodiment, the agent stimulating dermal or epidermal macromolecular synthesis is selected, for example and not restricted to, from the group formed by agents stimulating collagen synthesis, agents stimulating elastin synthesis, agents stimulating decorin synthesis, agents stimulating laminin synthesis, agents stimulating chaperone synthesis, agents stimulating hyaluronic acid synthesis, agents stimulating aquaporin synthesis, agents stimulating fibronectin synthesis, agents inhibiting collagen degradation, agents inhibiting elastin degradation, agents inhibiting serine proteases such as leukocyte elastase or cathepsin G, agents stimulating fibroblast proliferation, agents stimulating adipocyte proliferation, agents stimulating adipocyte differentiation, agents stimulating angiogenesis, agents stimulating glycosaminoglycan synthesis, DNA repair agents and/or DNA protecting agents, for example and not restricted to, extracts of *Centella asiatica, Saccharomyces cerevisiae, Solanum tuberosum, Rosmarinus officinalis, Vaccinium angustifolium*, extract of the algae *Macrocystis pyrifera, Padina pavonica*, extract of the plants soy, malt, flax, sage, red clover, kakkon-to, white lupin, hazelnut extract, corn extract, yeast extract, extract of beech tree shoots, extract of leguminosae seeds, extract of plant hormones such as gibberellins, auxins or cytokinins among others, or extract of zooplankton Salina, the product of milk fermentation with *Lactobacillus Bulgaricus*, asiaticosides and derivatives thereof, vitamin C and derivatives thereof, cinnamic acid and derivatives thereof, Matrixyl® [INCI: Palmitoyl Pentapeptide-3], Matrixyl® 3000 [INCI: Palmitoyl Tetrapeptide-3, Palmitoyl Oligopeptide] or Biopeptide CL™ [INCI: Glyceryl Polymethacrylate, Propylene Glycol, Palmitoyl Oligopeptide] marketed by Sederma, Antarcticine® [INCI: Pseudomonas Ferment Extract], Decorinyl® [INCI: Tripeptide-10 Citrulline], Serilesine® [INCI: Hexapeptide-10], Lipeptide [INCI: Hydrolized vegetable protein], Aldenine® [INCI: Hydrolized Wheat Protein, Hydrolized Soy Protein, Tripeptide-1], Peptide AC29 [INCI: Acetyl Tripeptide-30 Citrulline], acetyl-arginyl-phenylglycyl-tryptophyl-phenylglycine, acetyl-arginyl-phenylglycyl-valyl-glycine or acetyl-arginyl-phenylglycyl-valyl-phenyl-glycine marketed by Lipotec, Drieline® PF [INCI:Yeast Betaglucan] marketed by Alban Muller, Phytovityl C® [INCI: Aqua, Zea Mays Extract] marketed by Solabia, Collalift® [INCI: Hydrolyzed Malt Extract] marketed by Coletica/Engelhard, Phytocohesine® PSP [proposed INCI: Sodium Beta-Sitosterol Sulfate] marketed by Seporga, minerals such as calcium among others, retinoids and derivatives thereof, isoflavonoids, carotenoids, in particular lycopene, pseudodipeptides, retinoids and derivatives thereof such as retinol or retinyl palmitate among others, or heparinoids among others.

In a particular embodiment, the agent stimulating dermal or epidermal macromolecular synthesis is selected, for example and not restricted to, from the group formed by agents stimulating collagen synthesis, agents stimulating elastin synthesis, agents stimulating decorin synthesis, agents stimulating laminin synthesis, agents stimulating chaperone synthesis, agents stimulating hyaluronic acid synthesis, agents stimulating aquaporin synthesis, agents stimulating fibronectin synthesis, agents inhibiting collagen degradation, agents inhibiting elastin degradation, agents inhibiting serine proteases such as leukocyte elastase or cathepsin G, agents stimulating fibroblast proliferation, agents stimulating adipocyte proliferation, agents stimulating adipocyte differentiation, agents stimulating angiogenesis, agents stimulating glycosaminoglycan synthesis, DNA repair agents and/or DNA protecting agents, for example and not restricted to, extracts of *Centella asiatica, Saccharomyces cerevisiae, Solanum tuberosum, Rosmarinus officinalis, Vaccinium angustifolium*, extract of the algae *Macrocystis pyrifera, Padina pavonica*, extract of the plants soy, malt, flax, sage, red clover, kakkon-to, white lupin, hazelnut extract, corn extract, yeast extract, extract of beech tree shoots, extract of leguminosae seeds, extract of plant hormones such as gibberellins, auxins or cytokinins among others, or extract of zooplankton Salina, the product of milk fermentation with *Lactobacillus Bulgaricus*, asiaticosides and derivatives thereof, vitamin C and derivatives thereof, cinnamic acid and derivatives thereof, Matrixyl® [INCI: Palmitoyl Pentapeptide-3], Matrixyl® 3000 [INCI: Palmitoyl Tetrapeptide-3, Palmitoyl Oligopeptide] or Biopeptide CL™ [INCI: Glyceryl Polymethacrylate, Propylene Glycol, Palmitoyl Oligopeptide] marketed by Sederma, Antarcticine® [INCI: Pseudomonas Ferment Extract], Decorinyl® [INCI: Tripeptide-10 Citrulline], Serilesine® [INCI: Hexapeptide-10], Lipeptide [INCI: Hydrolized vegetable protein], Aldenine® [INCI: Hydrolized Wheat Protein, Hydrolized Soy Protein, Tripeptide-1], Peptide AC29 [INCI: Acetyl Tripeptide-30 Citrulline], acetyl-arginyl-phenylglycyl-tryptophyl-phenylglycine, acetyl-arginyl-phenylglycylvalyl-glycine or acetyl-arginyl-phenylglycyl-valyl-phenylglycine marketed by Lipotec, Drieline® PF [INCI:Yeast Betaglucan] marketed by Alban Muller, Phytovityl C® [INCI: Aqua, Zea Mays Extract] marketed by Solabia, Collalift® [INCI: Hydrolyzed Malt Extract] marketed by Coletica/Engelhard, Phytocohesine® PSP [proposed INCI: Sodium Beta-Sitosterol Sulfate] marketed by Seporga, minerals such as calcium among others, retinoids and derivatives thereof, isoflavonoids, carotenoids, in particular lycopene, pseudodipeptides, retinoids and derivatives thereof such as retinol or retinyl palmitate among others, or heparinoids among others.

In a particular embodiment, the elastase-inhibiting agent is selected, for example and not restricted to, from the group formed by Elhibin® [INCI: *Glycine Soja* (Soybean) Protein], Preregen® [INCI: Glycine Soja (soybean) Protein, Oxido Reductases] or Regu®-Age [INCI:Hydrolyzed Rice Bran Protein, *Glycine Soja* (Soybean) Protein, Oxido Reductases] marketed by Pentapharm/DSM, Juvenesce [INCI: Ethoxydiglicol and caprylic Triglycerid, Retinol, Ursolic Acid, Phytonadione, llomastat], Micromerol™ [INCI: *Pyrus Malus* Extract], Heather Extract [INCI: Calluna Vulgaris Extract], Extracellium®. [INCI: Hydrolyzed Potato Protein] or Flavagrum™ PEG [INCI: PEG-6 Isostearate, Hesperetin Laurate] marketed by Coletica/Engelhard/BASF, Proteasyl® TP LS8657 [INCI: *Pisum Sativum* Extract] marketed by Laboratoires Serobiologiques/Cognis, acetyl-arginyl-phenylglycyl-tryptophyl-phenylglycine, acetyl-arginyl-phenylglycyl-valyl-glycine or acetyl-arginyl-phenylglycyl-valyl-phenylglycine marketed by Lipotec, Sepilift DPHP [INCI: Dipalmitoyl hydroxyproline] marketed by SEPPIC, Vitaderm® [INCI: Alcohol, Water, Glycerin, Hydrolyzed Rice Protein, Ilex Aquifolium Extract, Sodium Ursolate, Sodium Oleanolate] marketed by Rahn, Gatuline® Age Defense 2 [INCI: Juglans Regia (Walnut) Seed Extract] marketed by Gattefosse, IP 2000 [INCI: Dextran, Trifluoroacetyl Tripeptide-2] marketed by IEB and Atrium, Radicaptol [INCI: Propylene Glycol, Water, *Passiflora Incarnata* Flower Extract, Ribes Nigrum (Blackcurrant) Leaf Extract, Vitis Vinifera (grape) Leaf Extract] marketed by Solabia or ViaPure™ *Boswellia* [INCI: Olivanum (*Boswellia Serrata*) Extract] marketed by Soliance, among others.

In a particular embodiment, the matrix metalloproteinase-inhibiting agent is selected, for example and not restricted to, from the group formed by ursolic acid, isoflavones such as genistein, quercetin, carotenoids, lycopene, soy extract, cranberry extract, rosemary extract, *Trifolium pratense* (red clover) extract, *Phormium tenax* (New Zealand flax) extract, kakkon-to extract, sage extract, retinol and derivatives thereof, retinoic acid and derivatives thereof, sapogenins such as diosgenin, hecogenin, smilagenin, sarsapogenin, tigogenin, yamogenin and yucagenin among others, Collalift® [INCI: Hydrolyzed Malt Extract], Juvenesce [INCI: Ethoxydiglicol and Caprylic Triglyceride, Retinol, Ursolic Acid, Phytonadione, Ilomastat] or EquiStat [INCI *Pyrus Malus Fruit Extract*, Glycine Soja Seed Extract] marketed by Coletica/Engelhard, Pepha®-Timp [INCI: Human Oligopeptide-20], Regu-Age [INCI: Hydrolyzed Rice Bran Protein, Glycine Soja Protein, Oxido Reductases] or Colhibin [INCI: Hydrolyzed Rice Protein] marketed by Pentapharm, Lipeptide [INCI: Hydrolized vegetable protein] or Peptide AC29 [INCI: Acetyl Tripeptide-30 Citrulline] marketed by Lipotec, Litchiderm™ [INCI: Litchi Chinensis pericarp extract] or Arganyl™ [INCI: Argania Spinosa Leaf Extract] marketed by Laboratories Serobiologiques/Cognis, MDI Complex® [INCI: glycosaminoglycans] or ECM-Protect® [INCI: Water (Aqua), Dextran, Tripeptide-2] marketed by Atrium Innovations, Dakaline [INCI: *Prunus amygdalus dulcis, Anogeissus leiocarpus* bark extract] marketed by Soliance, Homeostatine [INCI: *Enteromorpha compressa, Caesalpinia Spinosa*] marketed by Provital, Timp-Peptide [proposed INCI: Acetyl Hexapeptide] or ECM Moduline [proposed INCI: Palmitoyltripeptide] marketed by Infinitec Activos, IP2000 [INCI: Dextran, Trifluoroacetyl tripeptide-2] marketed by Institut Europeen de Biologie Cellulaire, Actimp 1.9.3® [INCI: Hydrolyzed Lupine Protein] marketed by Expanscience Laboratories, Vitaderm® [INCI: Alcohol, Water (Aqua), Glycerin, Hydrolyzed Rice Protein, Ilex Aquifolium Extract, Sodium Ursolate, Sodium Oleanolate] marketed by Rahn, adapalene, tetracyclines and derivatives thereof such as minocycline, rolitetracycline, chlortetracycline, metacycline, oxytetracycline, doxycycline, demeclocycline and their salts, Batimastat [BB94; [4-(N-hydroxyamino)-2R-isobutyl-3S-(thiophene-2-ylthiomethyl) succinyl]-L-phenylalanine-N-methylamide], Marimastat [BB2516; [2S—[N4(R*),2R*,3S]]—N4[2,2-dimethyl-1-[methylaminocarbonyl]propyl]-N1,2-dihydroxy-3-(2-methylpropyl)butanediamide], among others.

In a particular embodiment, the firming and/or redensifying and/or restructuring agent is selected, for example and not restricted to, from the group formed by extracts of *Malpighia punicitolia, Cynara scolymus, Gossypium herbaceum, Aloe Barbadensis, Panicum miliaceum, Morus nigra, Sesamum indicum, Glycine soja, Triticum vulgare*, Pronalen® Refirming HSC [INCI: *Triticum vulgare, Silybum Marianum, Glycine Soy, Equisetum Arvense, Alchemilla Vulgaris, Medicago Sativa, Raphanus Sativus*] or Polyplant® Refirming [INCI: Coneflower, Asiatic Centella, Fucus, Fenugreek] marketed by Provital, Lanablue® [INCI: Sorbitol, Algae Extract] marketed by Atrium Innovations, Pepha®-Nutrix [INCI: Natural Nutrition Factor] marketed by Pentapharm, or vegetable extracts which contain isoflavones, Biopeptide EL™ [INCI: Palmitoyl Oligopeptide], Biopeptide CL™ [INCI: Palmitoyl Oligopeptide], Vexel® [INCI: Water (Aqua), Propylene Glycol, Lecithin, Caffeine, Palmitoyl Carnitine], Matrixyl® [INCI: Palmitoyl Pentapeptide-3], Matrixyl® 3000 [INCI: Palmitoyl Tetrapeptide-3, Palmitoyl Oligopeptide] or Bio-Bustyl™ [INCI: Glyceryl Polymethacrylate, Rahnella Soy Protein Ferment, Water (Aqua), Propylene Glycol, Glycerin, PEG-8, Palmitoyl Oligopeptide] marketed by Sederma, Dermosaccharides® HC [INCI: Glycerin, Water (Aqua), Glycosaminoglycans, Glycogen], Aglycal® [INCI: Mannitol, Cyclodextrin, Glycogen, Aratostaphylos *Uva Ursi Leaf Extract*], Cytokinol® LS [INCI: Hydrolyzed Casein, Hydrolyzed Yeast Protein, Lysine HCL] or Firmiderm® LS9120 [INCI: *Terminalia Catappa* Leaf extract, *Sambucus Negra* Flower Extract, PVP, Tannic Acid] marketed by Laboratoires Serobiologiques/Cognis, Liftline® [INCI: Hydrolyzed wheat protein], Raffermine® [INCI: Hydrolyzed Soy Flour] or Ridulisse C® [Hydrolyzed Soy Protein] marketed by Silab, Serilesine® [INCI: hexapeptide-10], Decorinyl™ [INCI: Tripeptide-10 Citrulline], Trylagen® [INCI: *Pseudoalteromonas* Ferment Extract, Hydrolyzed Wheat Protein, Hydrolyzed Soy Protein, Tripeptide-10 Citrulline, Tripeptide-1], marketed by Lipotec, Ursolisome® [INCI: Lecithin, Ursolic Acid, Atelocollagen, Xanthan Gum, Sodium Chondroitin Sulfate] or Collalift® [INCI: Hydrolyzed Malt Extract] marketed by Coletica/Engelhard, Syn®-Coll [INCI: Palmitoyl Tripeptide-5] marketed by Pentapharm, Hydriame® [INCI: Water (Aqua), Glycosaminoglycans, Sclerotium Gum] marketed by Atrium Innovations or IP2000 [INCI: Dextran, Trifluoroacetyl tripeptide-2] marketed by Institut Europeen de Biologie Cellulaire among others.

In a particular embodiment, the anti-glycation agent is selected, for example and not restricted to, from the group formed by *Vaccinium angustifolium* extracts, ergothioneine and derivatives thereof, lysine, Aldenine® [INCI: Hydrolized Wheat Protein, Hydrolized Soy Protein, Tripeptide-1], -Vilastene™ [INCI: Lysine HCl, Lecithin, Tripeptide-10 Citrulline], dGlyage™ [INCI: Lysine HCl, Lecithin, Tripeptide-9 Citrulline] or Eyeseryl® [INCI: Acetyl Tetrapeptide-5] marketed by Lipotec, hydroxystilbenes and derivatives thereof, resveratrol or 3,3',5,5'-tetrahydroxystilbene among others.

In a particular embodiment, the free radical scavenger and/or anti-atmospheric pollution agent, and/or reactive carbonyl species scavenger is selected, for example and not restricted to, from the group formed by tea extract, olive leaf extract, *Rosmarinus officinalis* extract or *Eichhornia crassipes* extract, benzopyrenes, vitamin C and derivatives—thereof, vitamin E and derivatives thereof, in particular tocopherol acetate, ascorbyl glycoside, phenols and polyphenols, in particular tannins, tannic acid and ellagic acid, gallocatechol, anthocyanins, chlorogenic acid, stilbenes, indoles, cysteine-containing amino acid derivatives, in particular N-acetylcysteine, ergothioneine, S-carboxymethylcysteine, chelating agents, in particular EDTA or ethylenediamines, carotenoids, bioflavonoids, ubiquinone, idebenone, catalase, superoxide dismutase, lactoperoxidase, glutathione peroxidase, glutathione, benzylidene camphor, pidolates, lignans, melatonin, oryzanol, carnosine and derivatives thereof, GHK [INCI: Tripeptide-1] and its salts and/or derivatives, Aldenine® [INCI: Hydrolized wheat protein, hydrolized soy protein, tripeptide-1], Preventhelia™ [INCI: Diaminopropionoyl Tripeptide-33] or Lipochroman-6 [INCI: Dimethylmethoxy Chromanol] marketed by Lipotec, among others.

In a particular embodiment, the 5α-reductase inhibiting agent is selected, for example and not restricted to, from the group formed by extract of *Cinnamommum zeylanicum, Laminaria saccharina, Spiraea u/maria, Nettle Root, Pygeum africanum, Avena Sativa, Serenoa repens*, extracts of the plants *Arnica montana, Cinchona succirubra, Eugenia catyophyllata, Humulus lupulus, Hypericum perforatum, Mentha piperita, Rosmarinus officinalis, Salvia officinalis, Thymus vulgaricus*, extract of plants of the genus *Silybum*, extract of plants which contain sapogenins and in particular extract of plants of the genus *Dioscorea*, retinoids and in particular retinol, sulfur and derivatives thereof, zinc salts and in particular lactate, gluconate, pidolate, carboxylate, salicylate or zinc cysteate, selenium chloride, vitamin B6, pyridoxine, caprylol glycine, sarcosine, finasteride, dutasteride, izonsteride, turosteride and their salts, among others.

Likewise, in another particular embodiment, the lysyl- and/or prolyl hydroxylase inhibiting agent is selected, for example and not restricted to, from the group formed by 2,4-diaminopyrimidine 3-oxide or 2,4-diamino-6-piperidinopyrimidine 3-oxide, among others.

In another particular embodiment, the defensin synthesis-stimulating agent is selected, for example and not restricted to, from the group formed by extracts of or hydrolyzed *Aloe Vera*, Roast amaranth, *Rehmannias radix*, arnica, gardenia, carrot, orange, peach, pineapple, mint, gentian, hibiscus flower, walnut tree leaf, calabaza, peony, quinoa, boldo, rough bindweed, sunflower, elderberry, seaweed, hydrolyzed corn, hydrolyzed soy, hydrolyzed rice, valine and its isomers and derivatives, calcium and its salts, α-MSH and fragments contained in the amino acid sequence of α-MSH, vitamin A and its derivatives and precursors, vitamin D3 and its derivatives, jasmonic acid, fumaric acid, malic acid, citric acid, ascorbic acid, lactic acid, acetic acid, adipic acid, tartaric acid, cinnamic acid, glutamic acid, succinic acid, inulin, alkyl glucosides, poly-D-glutamic acid, glycine, L-methionine, L-alanine, L-citrulline, lactoprotein, casein, lactoperoxidase, lysozyme, polyphenol, alkyl glucosides, *Lactobacillus* extract, fusobacteria extracts or non-photosynthetic and unfruitful filamentous bacteria, acetyl-glutamyl-methionyl-alanyl-isoleucine, acetyl-arginyl-phenylglycyl-phenylglycine or acetyl-arginyl-6-aminohexanoyl-alanine marketed by Lipotec, among others.

In another particular embodiment, the bactericidal and/or bacteriostatic agent and/or antimicrobial and/or germicidal agent and/or fungicidal agent and/or fungistatic agent and/or germ inhibitor is selected, for example and not restricted to, from the group formed by macrolides, pyranosides, calcium channel blockers, for example and not restricted to, cinnarizine and diltiazem; hormones, for example and not restricted to, estril, analogues thereof or thyroxine and/or its salts, caprylyl glycol, imidazolidinyl urea, methyl 4-hydroxybenzoate [INCI: methylparaben], ethyl 4-hydroxybenzoate [INCI: ethylparaben], propyl 4-hydroxybenzoate [INCI: propylparaben], butyl 4-hydroxybenzoate [INCI: butylparaben], isobutyl 4-hydroxybenzoate [INCI: isobutylparaben], 1,3-bis(hydroxymethyl)-5,5-dimethylimidazolidine-2,4-dione [INCI: DMDM Hydantoin], benzyl 4-hydroxybenzoate [INCI: benzylparaben], benzyl alcohol, dehydroacetic acid, benzoic acid, sorbic acid, salicylic acid, formic acid, propionic acid, 2-bromo-2-nitropropane-1,3-diol, 3-p-chlorophenoxy-1,2-propanodiol [INCI: chlorphenesin], dichlorobenzyl alcohol, iodopropynyl butylcarbamate, benzalkonium chloride, odor-absorbing fungicides such as zinc ricinoleate, cyclodextrins, benzethonium chloride, chlorhexidine, ethanol, propanol, 1,3-butanediol, 1,2-propylene glycol, undecylenic acid, dehydroacetic acid, N-methylmorpholine acetonitrile (MMA), isopropanol, methanol, 1,2-hexanediol, 1,2-octanediol, pentylene glycol, glycerin laurate, glycerin caprilate, glycerin caprate, benzoyl peroxide, chlorhexidine gluconate, triclosan and derivatives thereof, phenoxyethanol, terpinen-4-ol, α-terpineol, resorcinol, stiemycin, erythromycin, neomycin, clindamycin and its esters, tetracyclines, metronidazole, azelaic acid, tolnaftate, nystatin, clotrimazole, ketoconazole, derivatives of zinc such as zinc piritionate or trithionate, zinc oxide and zinc undecylenate, piroctone olamine, isothiazolinones, selenium sulfur, benzyl hemiformal, boric acid, sodium borate, 6,6-dibromo-4,4-dichloro-2,2'-methylenediphenol [INCI: bromochlorophene], 5-bromo-5-nitro-1,3-dioxane, tosyichloramide sodium [INCI: chloramine T], chloroacetamide, p-chlorom-cresol, 2-benzyl-4-chlorophenol [INCI: chlorophene], dimethyl oxazolidine, dodecyl dimethyl-2-phenoxyethyl ammonium bromide [INCI: domiphen bromide], 7-ethyl bicyclooxazolidine, hexetidine, glutaraldehyde, N-(4-chlorophenyl)-N-[4-chloro-3-(trifluoromethyl)phenyl]-urea [INCI: cloflucarban], 2-hydroxy-4-isopropyl-2,4,6-cycloheptatriene-1-one [INCI: Hinokitiol], isopropylmethylphenol, mercury salts, aluminum salts, nisin, phenoxyisopropanol, o-phenylphenol, 3-heptyl-2-[(3-heptyl-4-methyl-3H-thiazole-2-ylidene)methyl]-4-methylthiazole iodide [INCI: Quaternium-73], silver chloride, sodium iodide, thymol, undecylenic acid, diethylenetriaminepentaacetic acid, ethylenediaminetetraacetic acid and ethylenediaminetetraacetates, lactoperoxidase, glucose oxidase, lactoferrin, alkylaryl sulfonates, halogenated phenols, phenol mercury acetate and/or mixtures thereof, benzamidines, isothiazolines, derivatives of phthalimide, derivatives of pyridine, guanidines, quinolines, 1,2-dibromo-2,4-dicyanobutane, iodine-2-propylbutyl carbamate, iodine, tamed iodines, peroxo compounds, 4-chloro-3,5-dimethylphenol, 2,2'-methylene-bis(6-bromo-4-chlorophenol), 3-methyl-4-(1-methylethyl)phenol, 3-(4-chlorophenoxy)-1,2-propanediol, 3,4,4'-trichlorocarbanilide (TTC), thiamine essence, eugenol, farnesol, glycerin monolaurate, diglycerin monocaprinate, N-alkyl salicylic acid amides such as n-octyl salicylic acid amide or n-decyl salicylic acid amide, derivatives of halogenated xylene and cresol, such as p-chloro-meta-cresol or p-chloro-meta-xylene, extracts of *Allium sativum, Calendula officinalis, Chamomilla recutita, Echinacea Purpura, Hyssopus Officinalis, Melaleuca alternifolia* or tea tree oil, carnation essence, menthol and mint essence, among others.

Likewise, in another particular embodiment, the NO-synthase-inhibiting agent is selected, for example and not restricted to, from the group formed by extracts of the plants *Vitis vinifera, Olea europaea* or *Gingko biloba* among others.

In a particular embodiment, the desquamating agent and/or keratolytic agent and/or exfoliating agent is selected, for example and not restricted to, from the group formed by hydroxy acids and derivatives thereof, β-hydroxyacids, in particular salicylic acid and derivatives thereof, or gentisic acid; α-hydroxyacids and its salts, such as glycolic acid, ammonium glycolate, lactic acid, 2-hydroxyoctanoic acid, α-hydroxycaprylic acid, mandelic acid, citric acid, malic acid or tartaric acid; α- and β-hydroxybutyric acids; polyhydroxy acids such as gluconic acid, glucuronic acid or saccharic acid; keto acids such as pyruvic acid, glyoxylic acid; pyrrolidinecarboxylic acid; cysteic acid and derivatives; aldobionic acids; azelaic acid and derivatives thereof such as azeloyl diglycinate; ascorbic acid and derivatives thereof such as 6-O-palmitoylascorbic acid, ascorbyl glucoside, dipalmitoylascorbic acid, magnesium salt of ascorbic acid-2-phosphate (MAP), sodium salt of ascorbic acid-2-phosphate (NAP), ascorbyl tetraisopalmitate (VCIP); nicotinic acid, its esters and nicotinamide (also called vitamin B3 or vitamin PP); nordihydroguaiaretic acid; urea; oligofucoses; cinnamic acid; derivatives of jasmonic acid; hydroxy stilbenes such as resveratrol; *Saccarum officinarum* extract; enzymes involved in desquamation or degradation of the corneodesmosomes, such as glycosidases, stratum corneum chymotryptic enzyme (SCCE) or other proteases such as trypsin, chymotrypsin, sutilain, papain or bromelain; chelating agents such as ethylenediaminetetraacetic acid (EDTA), aminosulfonic compounds such as 4-(2-hydroxyethyl)piperazine-1-ethanesulfonic acid (HEPES) or sodium methylglycine diacetate (TRILON® M marketed by BASF); derivatives of 2-oxothiazolidine-4-carboxylic acid (procysteine); derivatives of sugars such as O-octanoyl-6-D-maltose and N-acetylglucosamine; chestnut extract (*Castanea sativa*) such as that marketed by SILAB under the name Recoverine® [INCI: Water (Aqua), Castanea Sativa Seed Extract]; opuntia extract (*Opuntia ficus-indica*) such as that marketed by SILAB as Exfolactive® [INCI: Hydrolyzed Opuntia Ficus Indica Flower Extract]; or Phytosphingosine SLC® [INCI: Salicyloyl Phytosphingosine] marketed by Degussa/Evonik, Peel-Moist [INCI: Glycerin, Papain, Calcium Pantothenate, Xanthan Gum, Caprylyl Glycol, Urea, Magnesium Lactate, Ethylhexylglycerin, Potassium Lactate, Serine, Alanine, Proline, Magnesium Chloride, Sodium Citrate]; extract or combination of extracts of *Saphora japonica*, papaya, pineapple, squash or yam, and/or mixtures thereof.

In another particular embodiment, the anti-inflammatory agent and/or analgesic agent is selected, for example and not restricted to, from the group formed by madecassoside extract, echinacea extract, amaranth seed oil, sandal wood oil, peach tree leaf extract, extract of *Aloe vera, Arnica montana, Artemisia vulgaris, Asarum maximum, Calendula officinalis, Capsicum, Centipeda cunninghamii, Chamomilla recutita, Crinum asiaticum, Hamamelis virginiana, Harpagophytum procumbens, Hypericum perforatum, Lilium candidum, Malva sylvestris, Melaleuca alternifolia, Origanum majorana, Origanum vulgare, Prunus laurocerasus, Rosmarinus officialis, Salix alba, Silybum marianum, Tanacetum parthenium, Thymus vulgaris, Uncaria guianensis* or *Vaccinum myrtillus*, mometasone furoate, prednisolone, nonsteroidal antiinflammatories including cyclooxygenase or lipoxygenase inhibitors, benzydamine, acetylsalicylic acid, rosmarinic acid, ursolic acid, derivatives of glycyrrhizinate, α-bisabolol, azulene and analogues, sericoside, ruscogenin, escin, scoline, rutin and analogues, hydrocortisone, clobetasol, dexamethasone, prednisone, paracetamol, amoxiprin, benorilate, choline salicylate, faislamine, methyl salicylate, magnesium salicylate, salsalate, diclofenac, aceclofenac, acemetacin, bromfenac, etodolac, indomethacin, oxamethacin, proglumetacin, sulindac, tolmetin, ibuprofen, dexibuprofen, carprofen, fenbufen, fenoprofen, flurbiprofen, ketoprofen, dexketoprofen, ketorolac, loxoprofen, naproxen, miroprofen, oxaprozin, pranoprofen, tiaprofenic acid, suprofen, mefenamic acid, meclofenamate, meclofenamic acid, flufenamic acid, tolfenamic acid, nabumetone, phenylbutazone, azapropazone, clofezone, kebuzone, metamizole, mofebutazone, oxyphenbutazone, phenazone, sulfinpyrazone, piroxicam, lornoxicam, meloxicam, tenoxicam, celecoxib, etoricoxib, lumiracoxib, parecoxib, rofecoxib, valdecoxib, nimesulide, naproxcinod, fluproquazone or licofelone, omega-3 and omega-6 fatty acids, morphine, codeine, oxycodone, hydrocodone, diamorphine, pethidine, tramadol, bupenorphine, benzocaine, lidocaine, chloroprocaine, tetracaine, procaine, amitriptyline, carbamazepine, gabapentin, pregabalin, bisabolol, Neutrazen™ [INCI: Water, Butylene Glycol, Dextran, Palmitoyl Tripeptide-8] marketed by Atrium Innovations/Unipex Group, Meliprene® [INCI: Dextran, Acetyl Heptapeptide-1] marketed by Institut Europeen de Biologie Cellulaire/Unipex Group, Skinasensyl™ [INCI: Acetyl Tetrapeptide-15] or Anasensyl™ [INCI: Mannitol, Ammonium Glycyrrhizate, Caffeine, *Hippocastanum* (Horse Chestnut) Extract] marketed by Laboratoires Serobiologiques/Cognis, Calmosensine™ [INCI: Acetyl Dipeptide-1] marketed by Sederma, coenzyme Q10 or alkyiglycerine ethers.

In addition, in another particular embodiment, the whitening or depigmenting agent is selected, for example and not restricted to, from the group formed by extracts of *Achillea millefolium, Aloe vera, Aradirachta indica, Asmuna japonica, Autocarpus incisus, Bidens pilosa, Broussonetia papyrifera, Chlorella vulgaris, Cimicifuga racemosa, Emblica officinalis, Glycyrrhiza glabra, Glycyrrhiza uralensis, Ilex purpurea, Ligusticum lucidum, Ligusticum wallichii, Mitracarpus scaber, Morinda citrifolia, Morus alba, Morus bombycis, Naringi crenulata, Prunus domesticus, Pseudostellariae radix, Rumex crispus, Rumex occidentalis, Sapindus mukurossi, Saxifragia sarmentosa, Scutellaria Galericulate, Sedum sarmentosum Bunge, Stellaria medica, Triticum Vulgare, Uva ursi* or *Whitania somnifera*, flavonoides, soy extract, lemon extract, orange extract, ginkgo extract, cucumber extract, geranium extract, gayuba extract, carob extract, cinnamon extract, marjoram extract, rosemary extract, clove extract, soluble liquorice extract or blackberry leaf extract, Lipochroman-6 [INCI: Dimethylmethoxy Chromanol] or Chromabright™ [INCI: Dimethylmethoxy Chromanyl Palmitate] marketed by Lipotec, Actiwhite™ LS9808 [INCI: Aqua, Glycerin, Sucrose Dilaurate, Polysorbate 20,

*Pisum sativum* (Pea) extract] or Dermawhite® NF LS9410 [INCI: Mannitol, Arginine HCl, Phenylalanine, Disodium EDTA, Sodium Citrate, Kojic Acid, Citric Acid, Yeast Extract] marketed by Laboratoires Serobiologiques/Cognis, Lumiskin™ [INCI: Caprylic/Capric Triglycerid, Diacetyl-Boldine], Melaclear™ [INCI: Glycerin, Aqua, Dithiaoctanediol, Gluconic acid, Sutilains, Beta-carotene], O.D.A.white™ [INCI: octadecendioic acid] or Etioline™ [INCI: Glycerin, Butylene Glycol, Arctostaphylos uva ursi Leaf Extract, Mitracarpus scaber Extract] marketed by Sederma, Sepiwhite™ MSH [INCI: Undecylenoyl Phenylalanine] marketed by Seppic, Achromaxyl [INCI: Aqua, *Brassica napus Extract*] marketed by Vincience, Gigawhite™ [INCI: Aqua, Glycerin, *Malva sylvestris* (Mallow) Extract, Mentha piperita Leaf Extract, Primula veris Extract, *Alchemilla vulgaris Extract, Veronica officinalis Extract, Melissa officinalis* Leaf Extract, Achillea millefolium Extract], Melawhite® [INCI: Leukocyte Extract, AHA] or Melfade®-J [INCI: Aqua, Arctostaphylos uva-ursi Leaf Extract, Glycerin, Magnesium Ascorbyl Phosphate] marketed by Pentapharm, Albatin® [INCI: Aminoethylphosphoric Acid, Butylene Glycol, Aqua] marketed by Exsymol, Tyrostat™-11 [INCI: Aqua, Glycerin, *Rumex occidentalis Extract*] or Melanostatine®-5 [INCI: Dextran, Nonapeptide-1] marketed by Atrium Innovations, arbutin and its isomers, kojic acid and derivatives thereof, ascorbic acid and derivatives thereof such as 6-O-palmitoylascorbic acid, ascorbyl glucoside, dipalmitoylascorbic acid, magnesium salt of ascorbic acid-2-phosphate (MAP), sodium salt of ascorbic acid-2-phosphate (NAP), ascorbyl glucoside or ascorbyl tetraisopalmitate (VCIP); retinol and derivatives thereof including tretinoin and isotretinoin, idebenone, hydroxybenzoic acid and derivatives thereof, niacinamide, liquiritin, resorcinol and derivatives thereof, hydroquinone, α-tocopherol, γ-tocopherol, azelaic acid, azeloyl diglycinate, resveratrol, linoleic acid, α-lipoic acid, dihydrolipoic acid, α-hydroxy acids, β-hydroxy acids, ellagic acid, ferulic acid, cinnamic acid, oleanolic acid, aloesin and its derivatives and/or serine protease inhibitors, for example and not restricted to, tryptase, trypsin or. PAR-2 inhibitors, among others.

In another particular embodiment, the melanin synthesis stimulating agent, propigmenting agent, self-tanning agent and/or melanocyte proliferation stimulating agent is selected, for example and not restricted to, from the group formed by extracts of *Citrus Aurantium Dulcis* Fruit, *Coleus forskohlii, Coleus Esquirolii, Coleus Scutellariodes, Coleus Xanthanthus, Ballota nigra, Ballota lanata, Ballota suavelens, Marrubium cylleneum, Cistus creticus, Amphiachyris amoena, Aster oharai, Otostegia fruticosa, Plectranthus barbatus, Halimium viscosum* or *Larix laricema*, dihydroxyacetone and derivatives thereof, sugars, for example and not restricted to, erythrulose, melanin and derivatives thereof including melanin polymers and derivatives of melanin with a low molecular weight which are soluble in water, forskolin and derivatives thereof including deacetylforskolin and isoforskolin, tyrosine and derivatives thereof including acetyl tyrosine, oleoyl tyrosine, 3-amino tyrosine and 3-nitrotyrosine, copper salts such as $CuCl_2$, carotenoids, canthaxanthins, polymers of dihydroxyindole carboxylic acid, 3,4-dihydroxybenzoic acid, 3-amino-4-hydroxybenzoic acid, aloin, emodin, alizarin, dihydroxyphenylalanine, 4,5-dihydroxynaphthalene-2-sulfonic acid, 3-dimethylaminophenol or p-aminobenzoic acid, Melatime™ [INCI: Acetyl Tripeptide-40] marketed by Lipotec, Heliostatine IS™ [INCI: *Pisum Sativum* Extract] marketed by Vincience/ISP, Vegetan [INCI: Dihydroxyacetone] or Vegetan Premium [INCI: Dihydroxyacetone, Melanin] marketed by Soliance, MelanoBronze [INCI: *Vitex Agnus* Castus Extract, Acetyl Tyrosine] marketed by Mibelle Biochemistry, Melitane® [INCI: Acetyl Hexapeptide-1] marketed by Institut Europeen de Biologie Cellulaire/Unipex Innovations, Actibronze® [INCI: Hydrolyzed Wheat Protein, Acetyl Tyrosine, Copper Gluconate] or Instabronze® [INCI: Dihydroxyacetone, Tyrosine] marketed by Alban Muller, Thalitan [INCI: Hydrolyzed Algin, Magnesium Sulfate, Manganese Sulfate] marketed by CODIF, Tyrosilane® [INCI: Methylsilanol Acetyltyrosine] marketed by Exsymol, Tyr-Excel™ [INCI: Oleoyl Tyrosine, Luffa Cylindrica Seed Oil, Oleic Acid] or Tyr-OI [INCI: Oleoyl Tyrosine, Butylene glycol, Oleic Acid] marketed by Sederma/Croda, Bronzing S.F. [proposed INCI: Butyryl Pentapeptide] marketed by Infinitec Activos or Biotanning® [INCI: Hydrolyzed Citrus Aurantium Dulcis Fruit Extract] marketed by Silab, among others.

In a particular embodiment, the anti-wrinkle and/or anti-aging agent is selected, for example and not restricted to, from the group formed by extracts of *Vitis vinifera, Rosa canina, Curcuma longa, Iris pallida, Theobroma cacao, Ginkgo biloba, Leontopodium Alpinum* or *Dunaliella salina*, Matrixyl® [INCI: Palmitoyl Pentapeptide-4], Matrixyl 3000® [INCI: Palmitoyl Tetrapeptide-7, Palmitoyl Oligopeptide], Essenskin™ [INCI: calcium hydroxymethionine], Renovage [INCI: teprenone] or Dermaxyl® [INCI: Palmitoyl Oligopeptide] marketed by Sederma, Vialox® [INCI: Pentapeptide-3], Syn®-Ake® [INCI: Dipeptide Diaminobutyroyl Benzylamide Diacetate], Syn®-Coll [INCI: Palmitoyl Tripeptide-5], Phytaluronate [INCI: Locust Bean (*Ceratonia Siliqua*) Gum] or Preregen® [INCI: Glycine Soja (Soybean) Protein, Oxido Reductases] marketed by Pentapharm/DSM, Myoxinol™ [INCI: Hydrolyzed Hibiscus Esculentus Extract], Syniorage™ [INCI: Acetyl Tetrapeptide-11], Dermican™ [INCI: Acetyl Tetrapeptide-9] or DN-AGE™ LS [INCI: Cassia Alata leaf Extract] marketed by Laboratoires Serobiologiques/Cognis, Algisum C® [INCI: Methylsilanol Mannuronate] or Hydroxyprolisilane CN® [INCI: Methylsilanol Hydroxyproline Aspartate] marketed by Exsymol, Argireline® [INCI: Acetyl Hexapeptide-8], SNAP-7 [INCI: Acetyl Heptapeptide-4], SNAP-8 [INCI: Acetyl Octapeptide-3], Leuphasyl® [INCI: Pentapeptide-18], Aldenine® [INCI: Hydrolized wheat protein, hydrolized soy protein, Tripeptide-1], Preventhelia™ [INCI: Diaminopropionoyl Tripeptide-33], Decorinyl™ [INCI: Tripeptide-10 Citrulline], Trylagen® [INCI: *Pseudoalteromonas* Ferment Extract, Hydrolyzed Wheat Protein, Hydrolyzed Soy Protein, Tripeptide-10 Citrulline, Tripeptide-1], Eyeseryl® [INCI: Acetyl Tetrapeptide-5], Peptide AC29 [INCI: Acetyl Tripeptide-30 Citrulline], Lipochroman-6 [INCI: Dimethylmethoxy Chromanol], Chromabright™ [INCI: Dimethylmethoxy Chromanyl Palmitate], Antarcticine® [INCI: *Pseudoalteromonas* Ferment Extract], Vilastene™ [INCI: Lysine HCl, Lecithin, Tripeptide-10 Citrulline], dGlyage™ [INCI: Lysine HCl, Lecithin, Tripeptide-9 Citrulline], acetyl-arginyl-phenylglycyl-tryptophyl-phenylglycine, acetyl-arginyl-phenylglycyl-valyl-glycine or acetyl-arginyl-phenylglycyl-valyl-phenylglycine, Inyline™ [INCI: Acetyl Hexapeptide-30] marketed by Lipotec, Kollaren® [INCI: Tripeptide-1, Dextran] marketed by Institut Europeen de Biologie Cellulaire, Collaxyl® IS [INCI: Hexapeptide-9], Laminixyl IS™ [INCI: Heptapeptide], Orsirtine™ GL [INCI: Oryza Sativa (Rice) Extract], D'Orientine™ IS [INCI: Phoenix Dactylifera (Date) Seed Extract], Phytoquintescine™ [INCI: Einkorn (*Triticum Monococcum*) Extract] or Quintescine™ IS [INCI: Dipeptide-4] marketed by Vincience/ISP, BONT-L-Peptide [INCI: Palmitoyl Hexapeptide-19] marketed by Infinitec Activos, Deepaline™ PVB [INCI: Palmitoyl hydrolyzed Wheat Protein] or Sepilift® DPHP [INCI: Dipalmitoyl Hydroxyproline] marketed by Seppic, Gatuline® Expression [INCI: *Acmella oleracea* Extract], Gatuline® In-Tense [INCI: Spilanthes Acmella Flower Extract] or Gatuline® Age Defense 2 [INCI: Juglans Regia (Walnut) Seed Extract] marketed by Gattefossé, Thalassine™ [INCI: Algae Extract] marketed by Biotechmarine, ChroNOline™ [INCI: Caprooyl Tetrapeptide-3] or Thymulen-4 [INCI: Acetyl Tetrapeptide-2] marketed by Atrium Innovations/Unipex Group, EquiStat [INCI: Pyrus Malus Fruit Extract, Glycine Soja Seed Extract] or Juvenesce [INCI: Ethoxydiglicol and Caprylic Triglycerid, Retinol, Ursolic Acid, Phytonadione, Ilomastat] marketed by Coletica, Ameliox [INCI: Carnosine, Tocopherol, Silybum Marianum Fruit Extract] or PhytoCellTec Malus Domestica [INCI: Malus Domestica Fruit Cell Culture] marketed by Mibelle Biochemistry, Bioxilift [INCI: Pimpinella Anisum Extract] or SMS Anti-Wrinkle® [INCI: Annona Squamosa Seed Extract] marketed by Silab, $Ca^{2+}$ channel blockers, for example and not restricted to, alverin, manganese or magnesium salts, certain secondary or tertiary amines, retinol and derivatives thereof, resveratrol, idebenone, coenzyme Q10 and derivatives thereof, boswellic acid and derivatives thereof, GHK and derivatives thereof and/or salts, carnosine and derivatives thereof, DNA repair enzymes, for example and not restricted to, photolyase or T4 endonuclease V, or chloride channel blockers among others.

In a particular embodiment, the lipolytic agent or agent stimulating lipolysis, venotonic agent and/or anti-cellulite agent is selected, for example and not restricted to, from the group formed by extracts of *Bupleurum Chinensis, Cecropia Obtusifolia, Celosia Cristata, Centella Asiatica, Chenopodium Quinoa, Chrysanthellum Indicum, Citrus Aurantium Amara, Coffea Arabica, Coleus Forskohlii, Commiphora Myrrha, Crithmum Maritimum, Eugenia Caryophyllus, Ginkgo Biloba, Hedera Helix* (ivy extract), *Hibiscus Sabdariffa, Ilex Paraguariensis, Laminaria Digitata, Nelumbium Speciosum, Paullinia Cupana, Peumus Boldus, Phyllacantha Fibrosa, Prunella Vulgaris, Prunus Amygdalus Dulcis, Ruscus Aculeatus* (Butcherbroom extract), *Sambucus Nigra, Spirulina Platensis* Algae, *Uncaria Tomentosa* or *Verbena Officinalis*, dihydromyricetin, coenzyme A, lipase, glaucine, esculin, visnadine, Regu®-Shape [INCI: Isomerized Linoleic Acid, Lecithin, Glycerin, Polysorbate 80] marketed by Pentapharm/DSM, UCPeptide™ V [INCI: Pentapeptide] or AT Peptide™ IS [INCI: Tripeptide-3] marketed by Vincience/ISP, Liporeductyl® [INCI: Caffeine, Butcherbroom (*Ruscus Aculeatus*) Root Extract, TEA-Hydroiodide, Carnitine, Ivy (*Hedera Helix*) Extract, Escin, Tripeptide-1] marketed by Lipotec, Adiposlim [INCI: Sorbitan Laurate, Lauroyl Proline] marketed by SEPPIC, caffeine, carnitine, escin and/or triethanolamine iodide, among others.

In a particular embodiment, the heat shock protein synthesis stimulating agent is selected, for example and not restricted to, from the group formed by extracts of *Opuntia ficus indica, Salix alba, Lupinus* spp., *Secale cereale*, extracts of red algae from the genus *Porphyra*, extracts of crustaceans from the genus *Artemia*, jojoba seed oil, grape seed extracts, green tea extracts, geranylgeranylacetone, celastrol, zinc and its salts, 2-cyclopenten-1-one, proteasome inhibitors, for example and not restricted to, bortezomib; prostaglandins and derivatives thereof, hydroxylamine and derivatives thereof, for example and not restricted to, bimoclomol; chalcone and derivatives thereof, hyperosmotic agents, for example and not restricted to, sorbitol and derivatives thereof, mannitol and derivatives thereof or glycerol and derivatives thereof, isosorbide, urea or salicylic acid and derivatives thereof among others, or mixtures thereof.

In a particular embodiment, the hair growth inducing or hair loss retardant agent is selected, for example and not restricted to, from the group formed by the extracts of *Tussilago farfara* or *Achillea millefdlium*, nicotinic acid esters such as $C_3$-$C_6$ alkyl nicotinates such as methyl or hexyl nicotinate, benzyl nicotinate, or tocopheryl nicotinate; biotin, 5α-reductase-inhibiting agents, anti-inflammatory agents, retinoids, for example and not restricted to, All-trans-retinoic acid or tretinoin, isotretinoin, retinol or vitamin A, and derivatives thereof, such as acetate, palmitate, propionate, motretinide, etretinate and zinc salt of trans-retinoic acid; anti-bacterial agents, calcium channel blockers, for example and not restricted to, cinnarizine and diltiazem; hormones, for example and not restricted to, estriol, its analogues or thyroxine, its analogues and/or salts; antiandrogenic agents, for example and not restricted to, oxendolone, spironolactone or diethylstilbestrol; anti-radical agents, esterified oligosaccharides, for example and not restricted to, those described in documents EP 0211610 and EP 0064012; derivatives of hexasaccharide acids, for example and not restricted to, glucose-saccharide acid or those described in document EP 0375388; glucosidase inhibitors, for example and not restricted to, D-glucaro-1,5-lactam or those described in document EP 0334586; glycosaminoglycanase and proteoglycanase inhibitors, for example and not restricted to L-galactono-1,4-lactone or those described in document EP 0277428; tyrosine kinase inhibitors, for example and not restricted to, 1-amido-1-cyano(3,4-dihydroxyphenyl)ethylene or those described in document EP 0403238, diazoxides, for example and not restricted to, 7-(acetylthio)-4',5'-dihydrospiro[androst-4-ene-17,2'-(3H)furan]-3-one, 1,1-dioxide of 3-methyl-7-chloro[2H]-1,2,4-benzothiadiazine or spirooxazine; phospholipids, for example and not restricted to, lecithin; salicylic acid and derivatives thereof, hydroxycarboxylic or keto carboxylic acid and esters thereof, lactones and their salts; anthralin, eicose-5,8,11-trienoic acids and esters thereof or amides among others, minoxidil and derivatives thereof or mixtures thereof.

In another particular embodiment the body hair growth inhibiting or retardant agent is selected, for example and not restricted to, from the group formed by activin or activin agonists, flavonoids such as quercetin, curcumin, galangin, fisetin, myricetin, apigenin; propyl gallate, nordihydroguaiaretic acid, caffeic acid, tyrosine kinase inhibitors such as lavendustin, erbstatin; tyrphostins, benzoquinone-ansamycin herbimycin A, thiazolidinediones, phenazocine, 2,3-dihydro-2-thioxo-1H-indol-3-alcanoic acids, phenothiazine derivatives such as thioridazine; sphingosine and derivatives thereof, staurosporine and derivatives thereof, glycyrrhetinic acid, lauryl isoquinolinium bromide, Decelerine™ [INCI: Lauryl Isoquinolium Bromide, *Pseudoalteromonas* Ferment Extract] marketed by Lipotec or serine protease inhibitors, trypsin and/or mixtures thereof.

In a particular embodiment, the cosmetic and/or absorbent and/or body odor masking deodorant and/or antiperspirant agent, perfuming substance and/or perfumed oil is selected, for example and not restricted to, from the group formed by the complex zinc salt of ricinoleic acid, Styrax, derivatives of abiotic acid, sage essence, chamomile essence, carnation essence, lemon balm essence, mint essence, cinnamon leaf essence, lime flower essence, juniper berry essence, vetiver essence, olibanum essence, galbanum essence, labdanum essence, lavender essence, peppermint essence, bergamot orange, dihydromyrcenol, lilial, lyral, citronellol, lemon essence, mandarin essence, orange essence, lavender essence, muscat, geranium bourbon essence, aniseed, cilantro, cumin, juniper, extracts of fleur-de-lis, lilac, roses, jasmin, bitter orange blossom; benzyl acetate, p-tert-butyl-cyclohexyl acetate, linalyl acetate, phenylethyl acetate, ethylmethylphenyl glycinate, linalyl benzoate, benzyl formate, allyl cyclohexyl propionate, styrallyl propionate, benzyl salicylate, benzyl ethyl ether, linear alkanes with from 8 to 18 carbon atoms, citral, ricinoleic acid, citronellal, citronellyl oxyacetaldehyde, cyclamen aldehyde, hydroxycitronellal, bourgeonal, ionones, methyl cedryl ketone, anethole, eugenol, isoeugenol, geraniol, linalool, terpineol, phenylethyl alcohol, α-hexylcinnamaldehyde, geraniol, benzylacetone, cyclamen aldehyde, Boisambrene Forte®, ambroxan, indole, hedione, sandelice, cyclovertal, β-damascone, allyl amyl glycolate, dihydromyrcenol, phenoxyethyl isobutyrate, cyclohexyl salicylate, Vertofix Coeur, Iso-E-Super, Fixolide NP, Evernyl, phenylacetic acid, geranyl acetate, romillat, irotyl, floramate, active astringent products such as aluminum chloride, aluminum chlorohydrate, aluminum dichlorohydrate, aluminum sesquichlorohydrate, aluminum hydroxyallantoinate, aluminum chlorotartrate, aluminum and zirconium trichlorohydrate, aluminum and zirconium tetrachlorohydrate, aluminum and zirconium pentachlorohydrate and/or mixtures thereof.

In a particular embodiment, the antioxidant is selected, for example and not restricted to, from the group formed by butyihydroxytoluene (BHT), butylhydroxyanisole (BHA), tert-butylhydroquinone (TBHQ), 2,6,-di-tert-butyl-4-methylphenol, gallic acid esters such as propyl gallate, probucol, polyphenoles, ascorbic acid and its salts, enzymes such as catalase, superoxide dismutase and peroxidases; citric acid, citrates, monoglyceride esters, calcium metabisulfate, lactic acid, malic acid, succinic acid, tartaric acid, vitamin A or β-carotene, vitamins E and C, tocopherols such as vitamin E acetate, ascorbic acid esters such as ascorbyl palmitate and ascorbyl acetate, zinc, copper, mannitol, reduced glutathione, carotenoids such as cryptoxanthin, astaxanthin and lycopene; cysteine, uric acid, carnitine, taurine, tyrosine, lutein, zeaxanthin, N-acetyl-cysteine, carnosine, γ-glutamylcysteine, quercetin, lactoferrin, dihydrolipoic acid, tea catechins, retinyl palmitate and derivatives thereof, bisulfate, metabisulfite and sodium sulfite, chromans, chromens and their analogues, Lipochroman-6 [INCI: Dimethylmethoxy Chromanol], chelating agents of metals such as EDTA, sorbitol, phosphoric acid or dGlyage™ [INCI: Lysine HCl, Lecithin, Tripeptide-9 Citrulline]; extract of Ginkgo Biloba, plant extracts such as sage, pomegranate, rosemary, oregano, ginger, marjoram, cranberry, grape, tomato, green tea or black tea; oleoresin extract, extract of plants which contain phenols such as vanillin, ellagic acid and resveratrol; tertiary butylhydroquinone or mixtures thereof, metal salts with a valence of 2 such as selenium, cadmium, vanadium or zinc; a-lipoic acid, coenzyme Q, idebenone or derivatives thereof.

In a particular embodiment, the agent inhibiting sweat-degrading enzymes is selected, for example and not restricted to, from the group formed by trialkyl citrates such as trimethyl citrate, tripropyl citrate, triisopropyl citrate, tributyl citrate or triethyl citrate; lanosterine sulfate or phosphate, cholesterin, campesterin, stigmasterin and sitosterin; dicarboxylic acids and their esters, such as glutaric acid, monoethyl glutarate, diethyl glutarate, adipic acid, monoethyl adipate, diethyl adipate; malonic acid and diethyl malonate, hydroxycarboxylic acids and their esters such as malic acid, tartaric acid or diethyl tartrate, zinc glycinate and/or mixtures thereof.

In another particular embodiment, the agent capable of filtering UV rays is selected, for example and not restricted to, from the group formed by organic or mineral photoprotective agents active against A and/or B ultraviolet rays such as substituted benzotriazoles, substituted diphenylacrylates, organic nickel complexes, umbelliferone, urocanic acid, biphenyl derivatives, stilbene, 3-benzylidene camphor, and derivatives thereof such as 3-(4-methylbenzylidene)camphor; derivatives of 4-aminobenzoic acid, 2-ethylhexyl 4-(dimethylamino)benzoate, 2-octyl 4-(dimethylamino)benzoate and amyl 4-(dimethylamino)benzoate; cinnamic acid esters, such as 2-ethylhexyl 4-methoxycinnamate or diethylamino hydroxybenzoyl hexyl benzoate, propyl 4-methoxycinnamate, isoamyl 4-methoxycinnamate, 2-ethylhexyl (octocrylenes) 2-cyano-3,3-phenyl cinnamate; salicylic acid esters, such as 2-ethylhexyl salicylate, 4-isopropylbenzyl salicylate, homomenthyl salicylate; benzophenone derivatives, such as 2-hydroxy-4-methoxybenzophenone, 2-hydroxy-4-methoxy-4'-methylbenzophenone, 2,2'-dihydroxy-4-methoxybenzophenone; benzalmalonic acid esters, such as di-2-ethylhexyl 4-methoxybenzalmalonate; triazine derivatives, such as 2,4,6-trianilino, p-carbo-2'-ethyl-1'-hexyloxy-1,3,5-triazine, octyl triazone or dioctyl butamido triazones; propane-1,3-diones, such as 1-(4-tert-butylphenyl)-3-(4'-methoxyphenyl) propane-1,3-dione; ketotricyclo(5.2.1.0)decane derivatives; 2-phenylbenzimidazole-5-sulfonic acid; benzophenone sulfonic acid derivatives, such as 2-hydroxy-4-methoxybenzophenone-5-sulfonic acid and its salts; 4-(2-oxo-3-bornylidenemethyl)benzenesulfonic acid, benzoyl methane derivatives, such as benzoyl methane 2-methyl-5-(2-oxo-3-bornylidene)sulfonic acid, such as 1-(4'-tert-butylphenyl)-3-(4'-methoxyphenyl)propane-1,3-dione, 4-tert-butyl-4'-methoxydibenzoylmethane, 1-phenyl-3-(4'-isopropylphenyl)-propane-1,3-dione, enamine compounds, anthranilates, silicons, benzimidazole derivatives, imidazolines, benzoyl derivatives, Chromabright™ [INCI: Dimethylmethoxy Chromanyl Palmitate] or Preventhelia™ [INCI: Diaminopropionoyl Tripeptide-33] both marketed by Lipotec, metal oxides such as zinc oxide, titanium, iron, zirconium, silicon, manganese, aluminum and cerium; silicates, talc, barium sulfate, zinc stearate, carbon nanotubes and/or mixtures thereof.

In addition, in another particular embodiment, the agent stimulating or regulating keratinocyte differentiation is selected, for example and not restricted to, from the group formed by minerals such as calcium, retinoids such as retinol or tretinoin, analogues of vitamin D3 such as calcitriol, calcipotriol or tacalcitol, lupine (*Lupinus albus*) extract such as that marketed by SILAB under the name Structurin® [INCI: Hydrolyzed Lupine Protein], β-sitosterol sulfate, such as that marketed by Vincience/ISP under the name Phytocohesine PSP® [INCI: Sodium Beta-sitosterol Sulfate], maize (*Zea Mays*) extract such as that marketed by Solabia under the name Phytovityl C® [INCI: Water (Aqua), Zea Mays Extract], Helix Aspersa Müller glycoconjugates and/or mixtures thereof.

Likewise, in another particular embodiment, the muscle relaxant, agent inhibiting muscle contraction, agent inhibiting acetylcholine receptor clustering and/or anticholinergic agent is selected, for example and not restricted to, from the group formed by extracts of *Atropa belladonna, Hyoscyamus niger, Mandragora officinarum, Chondodendron tomentosum*, plants of the *Brugmansia* genus, or the *Datura* genus, *Clostridium botulinum* toxin, peptides derived from the protein SNAP-25 or Inyline™ [INCI: Acetyl Hexapeptide-30] marketed by Lipotec, baclofen, carbidopa, levodopa, bromocriptine, chlorphenesin, chlorzoxazone, donepezil, mephenoxalone, reserpine, tetrabenazine, dantrolene, thiocolchicoside, tizanidine, clonidine, procyclidine, glycopyrrolate, atropine, hyoscyamine, benztropine, scopolamine, promethazine, diphenhydramine, dimenhydrinate, dicyclomine, cyclobenzaprine, orphenadrine, flavoxate, cyclopentolate, ipratropium, oxybutynin, pirenzepine, tiotropium, trihexyphenidyl, tolterodine, tropicamide, solifenacin, darifenacin, mebeverine, trimethaphan, atracurium, cisatracurium, doxacurium, fazadinium, metocurine, mivacurium, pancuronium, pipecuronium, rapacuronium, tubocuranine, dimethyl tubocuranine, rocuronium, vecuronium, suxamethonium, 18-methoxycoronaridine, carisoprodol, febarbamate, meprobamate, metocarbamol, phenprobamate, tibamate, anticonvulsant agents such as levetiracetam, stiripentol, phenobarbital, methylphenobarbital, pentobarbital, metharbital, barbexaclone, pirimidone, carbamazepine, oxcarbazepine, benzodiazepines, for example and not restricted to, clonazepam, cloxazolam, clorazepate, diazepam, flutoprazepam, lorazepam, midazolam, nitrazepam, nimetazepam, phenazepam, temazepam, tetrazepam or clobazam, among others.

In another particular embodiment, the active ingredient is an insect repellent and is selected, for example and not restricted to, from the group formed by DEET (N,N-diethyl-meta-toluamide), ethyl hexanediol, dihydro-nepetalactone or a mixture of dihydronepetalactone stereoisomers, 3-methylbutanal, 2-methylbutanal, substituted hydroxy or amino methylbutanals; valeraldehyde and trans-pentenal, fenvalerate, esfenvalerate, 1S,3S,4S,6R-carene-3,4-diol, dipropyl pyridine-2,5-dicarboxylate, polytetrafluoroethylene, polyvinyl fluoride and vinylidene polyfluoride, dimethylsiloxane, polyvinyl chloride, vinylidene chloride, phthalic acid, dimethyl phthalate, dibutyl phthalate, polyethylene terephthalate, indalone (butyl-3,3-dihydro-2,2-dimethyl-4-oxo-2H-pyran-6-carboxylate), curcuma (*Curcuma longa*), bicyclic iridoid lactones, iridomyrmecin pheromones, sulfur, Epsom salts (hydrated calcium sulfate), pyrethrum or Dalmatian chrysanthemum (*Chrysanthemum cinerariaefolium*), lemon grass (*Cymbopogon nardus*), linalyl acetate, 1-limonene, cineole, eugenol, eugenyl acetate, piperidines such as picaridin or bayrepel (1-piperidinecarboxylic acid, 2-(2-hydroxyethyl)-1-methylpropyl ester) and its stereoisomers, 1-(3-cyclohexen-1-yl-carbonyl)-2-methylpiperidine and its stereoisomers, or ethyl butylacetylaminopropionate, 1-(3-cyclohexene-1-yl-carbonyl)piperidine, isoiridomyrmecin, 2,3,4,5-bis(2-butylene)tetrahydrofurfural, glycol butoxy polypropylene, N-butylacetanilide, dibutyl adipate, di-n-butyl succinate, dimethyl carbate (Endo, endo)-dimethyl-bicyclo[2.2.1] hept-5-ene-2,3-dicarboxylate, 2-ethyl-2-butyl-1,3-propanediol, 2-ethyl-1,3-hexanediol, propyl isocinchomeronate, 2-phenylcyclohexanol, normal-propyl N,N-diethyl succinamate, butyl mesityl oxide oxalate, 2-ethyl-1,3-hexanediol, N,N-diethylbenzamide, p-methane-3,8-diol, N,N-diethylmandelamide, isopulegol hydrate, ethyl-3-[N-n-butyl-N-acetyl] aminopropionate, diisopropyl adipate, alpha-biasabal, benzyl alcohol, N,N-diethyl phenylacetamide, vitamin E, 3-acetyl-2-(2,6-dimethyl-5-heptenyl) oxazolidine (2-hydroxymethylcyclohexyl)acetic acid lactone, tefluthrin, permethrin, cypermethrin, cyhalothrin, lambda-cyhalothrin, bifenthrin, deltamethrin, achiote or annatto oil (*Bixa orellana*), lemon leaves and fruit (*Citrus medica*), bitter almond oil, anise oil, basil oil, laurel oil, caraway seed oil, cardamom oil, cedar oil, celery oil, chamomile oil, spearmint oil, cinnamon oil, citronella oil, clove oil, cilantro oil, cumin oil, dill oil, eucalyptus oil, fennel oil, ginger oil, grape oil, lemon oil, mint oil, parsley oil, catnip oil, pepper oil, rose oil, mint oil (menthol), sweet orange oil, coconut oil, cedar oil, geraniol, geranium oil, thyme oil and curcuma oil.

It has previously been described that the colloids used in the first step of the process of this invention were hydrophilic, and in order for them to dissolve, the solvent should also be hydrophilic, such as water or an aqueous solution, as has also been previously described. The active ingredient or ingredients should be suspended in this solvent, as described in step a) of the process of the invention. However, this invention is not limited to lipophilic active ingredients suspended in a hydrophilic solvent. In a particular embodiment, in the case of hydrophilic active ingredients, the active ingredient is emulsified in a water in oil emulsion, W/O emulsion, and suspended in step a). In another particular embodiment, this W/O emulsion containing an active ingredient which is contained in turn in a solid lipid nanoparticle, SLN, or in a nanostructured lipid carrier, NLC, which is suspended in step a) of the process of the invention.

A second aspect of this invention relates to the fiber and/or textile material obtained according to the process of the invention. In this invention textile materials are understood to be woven fabrics, non-woven fabrics, garments and medical devices. Among the textile materials the preferred woven fabrics, non-woven fabrics, garments and medical devices are bandages, gauzes, t-shirts, socks, tights, underwear, girdles, gloves, diapers, sanitary napkins, dressings, bedspreads, wipes, hydrogels, adhesive patches, non-adhesive patches, micro-electric patches and/or face masks.

A third aspect of this invention relates to the use of the fibers and/or textile materials obtained according to the process of the invention for the treatment and/or care of the skin, hair and/or scalp. Preferably, the treatment and/or care of the skin, hair and/or scalp is selected from the group formed by the treatment and/or prevention of skin aging, healing of the skin and/or scalp, dermatological treatment of skin diseases, treatment and/or prevention of cellulitis, tanning of the skin, lightening of the color or bleaching of the skin and treatment and/or prevention of hair loss.

In the context of this invention, the term "aging" relates to the changes experienced by the skin with age (chronoaging) or due to exposure to the sun (photoaging) or to environmental agents such as tobacco smoke, extreme climatic conditions of cold or wind, chemical pollutants or pollution, and includes all the external visible changes as well as those noticeable by touch, for example and not restricted to, the development of discontinuities on the skin such as wrinkles, fine lines, furrows, irregularities or roughness, increase in the size of pores, loss of elasticity, loss of firmness, loss of smoothness, loss of the capacity to recover from the deformation, sagging of the skin such as sagging cheeks, the appearance of bags under the eyes or the appearance of a double chin among others, changes to the color of the skin such as marks, reddening, bags under the eyes, appearance of hyperpigmented areas such as age spots or freckles among others, anomalous differentiation, hyperkeratinization, elastosis, keratosis, hair loss, orange-peel skin, loss of collagen structure and other histological changes of the stratum corneum, of the dermis, epidermis, vascular system (for example the appearance of spider veins or telangiectasias) or of tissues close to the skin, among others.

The following specific examples provided herein serve to illustrate the nature of this invention. These examples are included solely for illustrative purposes and should not be construed as limitations on the invention claimed herein.

DESCRIPTION OF FIGURES

FIG. 1: FIG. 1 shows photographs by scanning electron microscopy for a treated polyamide fabric, example 6, to which the microcapsules of example 4 have been bound by foulard application. Part a) is an untreated polyamide, part b) a polyamide after 0 washes, part c) a polyamide after 5 washes.

EXAMPLES

General Methodology

All the reagents and solvents are of synthesis quality and are used without any additional treatment.

Example 1

Obtaining Cationized Microcapsules Containing Chromabright™ with Polyquaternium-16

Carboxymethyl cellulose was dissolved in water (phase B). Next, gelatin was dissolved in water (phase A) under stirring for 15 minutes and phase A was raised to boiling point. The bath was inserted at 75° C. and phase B was added to phase A and it was ensured that the temperature did not fall below 60° C. and that the pH of the mixture was between 5 and 5.5. The components for phase C were added under maximum stirring and a temperature above 60° C. The pH was lowered very slowly with the components from phase D until leaving it at approximately 4.43. It was stirred for 30 min and the pH was measured (4.42). The mixture was left to cool whilst being stirred for 2 hours and half way through the pH was measured (4.55) and was adjusted to 4.44 with the components from phase D. The pH was raised to 7.5 adding the components from phase E, and afterwards the components from phase F were added, a diluted crosslinker, and was stirred all night. The next day G was added as a cationic polymer and was stirred for 3 hours.

|   | INGREDIENT (INCI Nomenclature) | % IN WEIGHT |
|---|---|---|
| A | GELATIN (150B 30/40) | 2.4 |
| A | AQUA (WATER) | q.s.p. 100 |
| B | CELLULOSE GUM | 0.6 |
| B | AQUA (WATER) | 35.1 |
| C | BETA-CAROTENE | 1.00 |
| C | DIMETHYLMETHOXY CHROMANYL PALMITATE | 1.00 |
| C | MINERAL OIL (PARAFFINUM LIQUIDUM) | 8.00 |
| D | CITRIC ACID | 0.15 |
| D | AQUA (WATER) | 0.35 |
| E | SODIUM HYDROXIDE | 0.09 |
| E | AQUA (WATER) | 0.21 |
| F | GLUTARAL | 0.50 |
| F | AQUA (WATER) | 0.50 |
| G | POLYQUATERNIUM-16 | 15.0 |

Example 2 (Prophetic)

Obtaining Cationized Microcapsules Containing Inyline™ with Polyquaternium-16

First Inyline™ [INCI: Acetyl Hexapeptide-30] is dissolved in water and alcohol (phase C). Phase C is added to phase D little by little under stirring. These two phases together are added to soybean oil (phase E). Afterwards carboxymethylcellulose is dissolved in water (phase B). Next, gelatin is dissolved in water (phase A) and stirred for 15 minutes and phase A is raised to boiling point. The bath is inserted at 75° C. and phase B is added to phase A and it is ensured that the temperature does not fall below 60° C. and that the pH of the mixture is between 5 and 5.5. The mixture of phases C, D and E are added under maximum stirring and at a temperature above 60° C. The pH is lowered with the components from phase F very slowly until leaving it at approximately 4.43. It is stirred for 30 min and the pH is measured. The mixture is left to cool to room temperature whilst being stirred. The pH is raised to 7 adding the components of phase G, and afterwards the components of phase H and a diluted crosslinker are added and the mixture is stirred all night. The next day I is added as a cationic polymer and is stirred for 3 hours.

|   | INGREDIENT (INCI Nomenclature) | % IN WEIGHT |
|---|---|---|
| A | GELATIN (150B 30/40) | 2.4 |
| A | AQUA (WATER) | 30.10 |
| B | CELLULOSE GUM | 0.6 |
| B | AQUA (WATER) | 30.10 |
| C | ACETYL HEXAPEPTIDE-30 | 0.00004 |
| C | ALCOHOL DENAT. | 0.007 |
| C | AQUA (WATER) | q.s.p. 100 |
| D | DIOCTYL SULFOSUCCINATE | 0.013 |
| D | ISOESTEARIC ACID | 0.08 |
| E | SOYBEAN (*GLYCINE SOJA*) OIL | 10.00 |
| F | CITRIC ACID | 0.15 |
| F | AQUA (WATER) | 0.35 |
| G | SODIUM HYDROXIDE | 0.09 |
| G | AQUA (WATER) | 0.21 |
| H | GLUTARAL | 0.50 |
| H | AQUA (WATER) | 0.50 |
| I | POLYQUATERNIUM-16 | 15.0 |

Example 3

Obtaining Cationized Microcapsules Containing Argireline® with Polyquaternium-16

The Argireline® [INCI: Acetyl Hexapeptide-3] microcapsules were prepared in the same way as in example 2, but replacing Inyline™ [INCI: Acetyl Hexapeptide-30] with Argireline® [INCI: Acetyl Hexapeptide-3].

|   | INGREDIENT (INCI Nomenclature) | % IN WEIGHT |
|---|---|---|
| A | GELATIN (150B 30/40) | 2.4 |
| A | AQUA (WATER) | 30.10 |
| B | CELLULOSE GUM | 0.6 |
| B | AQUA (WATER) | 30.10 |
| C | ACETYL HEXAPEPTIDE-3 | 0.00025 |
| C | ALCOHOL DENAT. | 0.007 |
| C | AQUA (WATER) | q.s.p. 100 |
| D | DIOCTYL SULFOSUCCINATE | 0.013 |
| D | ISOESTEARIC ACID | 0.08 |
| E | SOYBEAN (*GLYCINE SOJA*) OIL | 10.00 |
| F | CITRIC ACID | 0.15 |
| F | AQUA (WATER) | 0.35 |
| G | SODIUM HYDROXIDE | 0.09 |
| G | AQUA (WATER) | 0.21 |
| H | GLUTARAL | 0.50 |
| H | AQUA (WATER) | 0.50 |
| I | POLYQUATERNIUM-16 | 15.0 |

Example 4

Obtaining Cationized Microcapsules Containing Antarcticine® and Vitamin E Acetate with Polyquaternium-16

The microcapsules were prepared in the same way as in example 1, substituting Chromabright™ with Antarcticine® [INCI: Pseudoalteromonas Ferment Extract] and vitamin E acetate.

| INGREDIENT (INCI Nomenclature) | % IN WEIGHT |
|---|---|
| A GELATIN (150B 30/40) | 2.4 |
| A PHENOXYETHANOL | 0.835 |
| A PROPANEDIOL | 4.175 |
| A AQUA (WATER) | q.s.p. 100 |
| B CELLULOSE GUM | 0.6 |
| B AQUA (WATER) | 30.00 |
| C PSEUDOALTEROMONAS FERMENT EXTRACT | 0.40 |
| C TOCOPHERYL ACETATE | 3.50 |
| C SOYBEAN (GLYCINE SOJA) OIL | 6.50 |
| D CITRIC ACID | 0.15 |
| D AQUA (WATER) | 1.00 |
| E SODIUM HYDROXIDE | 0.10 |
| E AQUA (WATER) | 10.00 |
| F GLUTARAL | 0.50 |
| F AQUA (WATER) | 0.50 |
| G POLYQUATERNIUM-16 | 15.0 |

Example 5

Textile Material Containing Antarcticine® and Vitamin E Acetate and Determination of the Quantity of Vitamin E Acetate After Several Washes.

The microcapsules from example 4 were bound. The link or binding of the microcapsules from example 4 to the textile materials was carried out by exhaustion bath. The textile materials were hung up to dry after the bath according to standard UNE-EN ISO 6330.

To test the washproofness of the microcapsules bound to the previous textile materials the latter were treated with detergent solutions under stirring according to standard ISO 105 C06. The textile materials were hung up to dry according to standard UNE-EN ISO 6330 after each wash. The determination of the quantity of microcapsules linked to the textile material was carried out determining by HPLC (Column: C18 Nucleosil 100A, 5 µm, 250×4.6 mm; water and methanol Mobile Phase, 0.7 mL/min flow, detection 290 nm) the quantity of active ingredient present in the textile material. The quantities of active ingredient bound to the textile material after the bath and after a number of washes were determined after the extraction of vitamin E acetate from the textile material by sonication for 10 minutes. The external phase was filtered (0.45 µm) and was analyzed by HPLC-UV/VIS detector. The percentages of vitamin E acetate present in the textile materials after five washes were an average of 66% with regards to the percentage of vitamin E initially linked.

Example 6

Textile Material Containing Antarcticine® and Vitamin E Acetate and Determination of the Quantity of Vitamin E Acetate After Several Washes.

The cationic microcapsules from example 4 were bound. The link or binding of the microcapsules from example 4 to the textile materials was carried out by foulard method (pressure 1 bar, binding at 150° C. for 2 minutes, 914 g of microcapsules from example 4 per 1000 l of bath). The textile materials were dried at 150° C. for 2 minutes.

To test the washproofness of the microcapsules bound to the previous textile materials the latter were treated with detergent solutions under stirring according to standard ISO I05 CO6. The textile materials were hung up to dry according to standard UNE-EN ISO 6330 after each wash. The determination of the quantity of microcapsules linked to the textile material was carried out determining by HPLC (Column: C18 Nucleosil 100A, 5 µm, 250×4.6 mm; water and methanol Mobile Phase, 0.7 mL/min flow, detection 290 nm) the quantity of active ingredient present in the textile material. The quantities of active ingredient bound to the textile material after the bath and after a number of washes were determined after the extraction of vitamin E acetate from the textile material by sonication for 10 minutes. The external phase was filtered (0.45 µm) and analyzed by HPLC-UV/VIS detector. The percentages of vitamin E acetate present with regards to the percentage of vitamin E initially linked are shown in the table below.

| % vitamin E | Polyamide | Cotton |
|---|---|---|
| 0 washes | 100 | 36 |
| 1 wash | 89 | 25 |
| 5 washes | 36 | 27 |
| 10 washes | 30 | 12 |
| 20 washes | 16 | |

The presence of microcapsules linked to the textile material was checked by scanning electron microscopy (see FIG. 1). For this the different textile materials were dehydrated in a desiccator for 48 hours, and coated with a fine gold laminate (200 Å). The microscope used was FEI Quanta-200, FEI Company, North America at 10 kV owned by the Scientific-Technical Services of the University of Barcelona.

The invention claimed is:

1. A process of treatment of fibers and/or textile materials which comprises the following steps:
   a) dissolution of two hydrophilic colloids in a solvent in which they are soluble and addition of at least one active ingredient to form a suspension of the active ingredient in this solution,
   b) adjusting the pH and/or diluting the previous suspension to cause coacervation of the colloids and their deposition on the active ingredient which is encapsulated,
   c) after b), increasing the pH of the suspension before adding a crosslinking agent to harden the microcapsules formed,
   d) cationizing the microcapsules with a cationic polymer or monomer,
   e) linking or binding of the microcapsules to the fibers and/or textile materials, and
   f) drying of the fibers and/or textile materials.

2. The process according to claim 1, which, additionally comprises the cooling of the microcapsules between step b) and step c).

3. The process according to claim 1, wherein the hydrophilic colloids are selected from the group formed by proteins, polysaccharides, polyesters, polycyanoacrylates, and mixtures thereof.

4. The process according to claim 3, wherein the proteins and polysaccharides are selected from the group formed by gelatin, albumin, β-lactoglobulin, whey protein, pea protein, potato protein, broad bean protein, wheat protein, bovine serum albumin, poly-L-lysine, soy protein, caseinates, casein, soy glycine, sodium alginate, wheat starch, corn starch, methyl cellulose, ethyl cellulose, hydroxypropyl methyl cellulose, cellulose nitrate, carboxymethyl cellulose, gum arabic, xanthan gum, mesquite gum, guar gum, carrageenans, tragacanth gum, arabinogalactans, galactomannans, sodium hexametaphosphate, exopolysaccharide B40, carboxymethyl sodium, pectin, methoxyl pectin, agar, dextran, chitosan, cellulose acetate butyrate, cellulose acetate phthalate, acrylic derivatives and polyesters such as poly-ϵ-caprolactone, zein, hydroxypropyl methylcellulose phthalate, hydroxypropyl methylcellulose acetate succinate, polyvinyl acetate phthalate, poly(p-dioxanone), poly(β-valerolactone), poly(β-hydroxybutyrate), poly(β-hydroxybutyrate) and β-hydroxyvalerate copolymers, poly (β-hydroxypropionate), methylacrylic acid copolymers, dimethylaminoethyl methacrylate copolymers, trimethylammonium ethyl methacrylate copolymers, polymers and copolymers of lactic and glycolic acid, polymers and copolymers of lactic and glycolic acid and polyethylene glycol and mixtures thereof.

5. The process according to claim 1, wherein the adjustment of the pH in step b) is to a pH between 3 and 5.5.

6. The process according to claim 1, wherein the increase of the pH in step c) is to a pH between 6.5 and 13.

7. The process according to claim 1, wherein the crosslinking agent is selected from the group formed by aldehydes, glutaraldehyde, formaldehyde, transglutaminases, derivatives of methylenebisacrylamide, N,N-methylenebisacrylamide, N,N-(1,2-dihydroxyethylene)bisacrylamide, derivatives of ethylene glycol dimethacrylate, ethylene glycol diacrylate, diethylene glycol diacrylate, tetraethylene glycol diacrylate, ethylene glycol dimethacrylate, diethylene glycol dimethacrylate, triethylene glycol dimethacrylate, sodium tripolyphosphate, N-hydroxysuccinamide esters and/or imidoesters.

8. The process according to claim 1, wherein the cationic polymer is selected from the group formed by cationic cellulose derivatives, quaternized hydroxyethylcellulose, cationic starches, diallyl ammonium and acrylamide salt copolymers, quaternized vinylpyrrolidone/vinylimidazole polymers, condensation products of polyglycols and amines, polyquaternium polymers and copolymers, polymers called Merquats of polyquaternium-6, polyquaternium-7, polyquaternium-16, polyquaternium-10, polyquaternium-4 copolymers, dicocoylethylhydroxyethylammonium, grafting copolymers with a cellulose skeleton and quaternary ammonium groups, quaternized collagen polypeptides, hydroxypropyllauryldimonium hydrolyzed collagen, quaternized wheat polypeptides, polyethylenimine, cationic silicone polymers, amidomethicone or silicone quaternium-22, adipic acid and dimethylamino hydroxypropyl diethylenetriamine copolymers, acrylic acid copolymers with dimethyldiallylammonium chloride, cationic chitin derivatives, condensation products of cationic dihalogen alkylene, condensation products of dibromobutane with bisdialkylamines, bis-dimethylamino-1,3-propane, derivatives of cationic guar gum, guar-hydroxypropyltrimonium, quaternary ammonium salt polymers, quaternized polysaccharide polymers of natural derivatives such as azarose, cationic gelatin proteins, cationic gum arabic proteins, cationic polyamide polymers, cationic polycyanoacrylate polymers, cationic polylactide polymers, cationic polyglycolides polymers, cationic polyaniline polymers, cationic polypyrrole polymers, cationic polyvinylpyrrolidone polymers, cationic polymers of amino silicone polymers and copolymers, cationic polystyrene polymers, cationic polyvinyl alcohol polymers, cationic polystyrene and maleic acid anhydride copolymers, cationic methyl vinyl ether polymers, cationic epoxy resin polymers, cationic polymers of styrene and methyl methacrylate copolymers, cationic polyacrylates and polymethacrylates, polyamine derivatives optionally substituted by derivative polyethylene glycol members, polyamino acids under pH conditions wherein they are cationic, polyethyleneimine, quaternized derivatives of polyvinylpyrrolidone and hydrophilic urethane polymers, as well as any mixture of the aforementioned cationic groups.

9. The process according to claim 1, wherein the linking or binding is carried out by exhaustion bath, or foulard, or spraying.

10. The process according to claim 1, wherein the drying is carried out for at least 2 minutes at temperatures higher than 100° C.

11. The process according to claim 1, wherein the active ingredient is selected from the group formed by active ingredients and/or cosmetic and/or dermopharmaceutical adjuvants and insect repellents.

12. The process according to claim 11, wherein the active ingredient and/or cosmetic and/or dermopharmaceutical adjuvant is selected from the group formed by surfactants, humectants or substances which retain moisture, moisturizers or emollients, agents stimulating healing, coadjuvant healing agents, agents stimulating re-epithelialization, coadjuvant re-epithelialization agents, agents which synthesize dermal or epidermal macromolecules, firming and/or redensifying and/or restructuring agents, cytokine growth factors, agents which act on capillary circulation and/or microcirculation, anti-glycation agents, free radical scavengers and/or anti-atmospheric pollution agents, reactive carbonyl species scavengers, 5α-reductase-inhibiting agents, lysyl- and/or prolyl hydroxylase inhibiting agents, defensin synthesis-stimulating agents, bactericidal agents and/or bacteriostatic agents and/or antimicrobial agents and/or germicidal agents and/or fungicidal agents and/or fungistatic agents and/or germ-inhibiting agents, anti-viral agents, antiparasitic agents, antihistaminic agents, NO-synthase inhibiting agents, desquamation agents or keratolytic agents and/or exfoliating agents, comedolytic agents, anti-psoriasis agents, anti-dandruff agents, anti-inflammatory agents and/or analgesics, anesthetic agents, anti-wrinkle and/or anti-aging agents, cosmetic deodorants and/or absorbent and/or body odor masking deodorants, antiperspirant agents, perfuming substances and/or perfumed oils and/or isolated aromatic compounds, anti-oxidizing agents, agents inhibiting vascular permeability, hydrolytic epidermal enzymes, whitening or skin depigmenting agents, agents inhibiting sweat-degrading enzymes, agents capable of filtering UV rays, agents which stimulate or regulate keratinocyte differentiation, anti-itching agents, agents which stimulate or inhibit the synthesis of melanin, propigmenting agents, self-tanning agents, agents stimulating the proliferation of melanocytes, liquid propellants, vitamins, amino acids, proteins, biopolymers, gelling polymers, skin relaxant agents, agents capable of reducing or treating bags under eyes, agents for the treatment and/or care of sensitive skin, astringent agents, agents regulating sebum production, anti-stretch mark agents, lipolytic agents or agents stimulating lipolysis, venotonic agents, anti-cellulite agents, calming agents, agents acting on cell metabolism, agents to improve dermal-epidermal junction, agents inducing hair growth or hair-loss retardants, body hair growth inhibiting or retardant agents, heat shock protein synthesis stimulating agents, muscle relaxants, muscle contraction inhibiting agents, agents inhibiting the aggregation of acetylcholine receptors, anticholinergic agents, elastase inhibiting agents, matrix metalloproteinase inhibiting agents, chelating agents, vegetable extracts, essential oils, marine extracts, mineral salts, cell extracts, emulsifying agents, agents stimulating the synthesis of lipids and components of the stratum corneum, agents obtained from a bio-fermentation process, and mixtures thereof.

13. The process according claim 1, wherein the active ingredient is emulsified in a water in oil emulsion and is suspended in step a).

14. The process according to claim 13, wherein the water in oil emulsion is contained in a solid lipid nanoparticle or in a nanostructured lipid carrier.

* * * * *